(12) United States Patent
Chou et al.

(10) Patent No.: US 7,678,384 B2
(45) Date of Patent: Mar. 16, 2010

(54) VINYLAMINOPYRAZOLE DERIVATIVES AS PESTICIDES

(75) Inventors: David Teh-Wei Chou, Bad Soden (DE); Maria Thönessen, Heidesheim (DE); Anke Kuhlmann, Leverkusen (DE); Uwe Döller, Rodgau (DE); Waltraud Hempel, Liederbach (DE)

(73) Assignee: Merial Limited, Duluth, GA (US)

( * ) Notice: Subject to any disclaimer, the term of this patent is extended or adjusted under 35 U.S.C. 154(b) by 57 days.

(21) Appl. No.: 11/747,293

(22) Filed: May 11, 2007

(65) Prior Publication Data

US 2008/0076802 A1    Mar. 27, 2008

Related U.S. Application Data

(63) Continuation-in-part of application No. PCT/EP2005/010403, filed on Sep. 27, 2005.

(30) Foreign Application Priority Data

Nov. 11, 2004   (EP)   ................... 04026768

(51) Int. Cl.
A01N 43/56 (2006.01)
A61K 31/415 (2006.01)
C07D 231/04 (2006.01)

(52) U.S. Cl. .................... 424/405; 514/407; 548/367.4; 548/369.1

(58) Field of Classification Search ................. 424/405; 514/407; 548/367.4, 369.1
See application file for complete search history.

(56) References Cited

U.S. PATENT DOCUMENTS 4,771,066 A * 9/1988 Gehring et al. ............. 514/404

FOREIGN PATENT DOCUMENTS

| DE | 3606476 A1 | 9/1987 |
| WO | WO9625401 A1 | 8/1996 |
| WO | WO 98/28277 | * 7/1998 |

* cited by examiner

*Primary Examiner*—David J Blanchard
*Assistant Examiner*—Kortney L Klinkel
(74) *Attorney, Agent, or Firm*—Judy Jarecki-Black; Merial Limited; Thomas Kowalski, Esq.

(57) ABSTRACT

Disclosed are 5-(vinylamino)pyryazole derivatives of formula I or pesticidally acceptable salts thereof (I) wherein, for example, W is =N—, =CH—, =CR$^6$— or =C(NH2)-, R$^6$ is halogen or haloalkyl, R$^1$ is cyano, halogen, alkyl, haloalkyl or —CS—NH2, R$^2$ is alkyl or cycloalkyl, R$^3$ is alkyl, alkenyl, alkynyl, cycloalkyl, aryl, heterocyclyl, aralkyl, heterocyclylalkyl, —CO—O—R$^9$, —CO—R$^{10}$, —SO—R", —SO$_2$—R$^{12}$; R$^9$, R$^{10}$, R$^{11}$ and R$^{12}$ are for example organic groups, R$^4$ is halogen or —NH$_2$, R$^5$ is haloalkyl, haloalkoxy, halogen or —SF$_5$, and n is an integer selected from 0, 1 or 2. These compounds cab be used for controlling pests, especially by treatment of domestic animals.

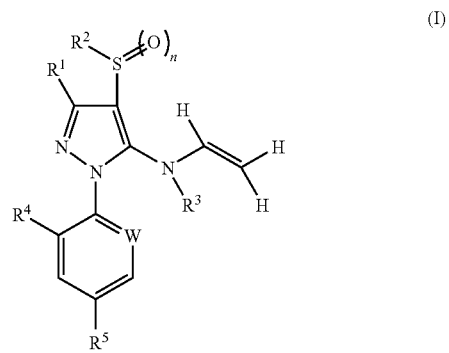

13 Claims, No Drawings

VINYLAMINOPYRAZOLE DERIVATIVES AS PESTICIDES

This application is a continuation-in-part application of international patent application Serial No. PCT/EP05/010403 filed Sep. 27, 2005, which published as PCT Publication No. WO 2006/050772 on May 18, 2006, which claims benefit of European patent application Serial No. 04026768.4 filed Nov. 11, 2004.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. Citation or identification of any document in this application is not an admission that such document is available as prior art to the present invention. It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention. The embodiments of the present invention are disclosed herein or are obvious from and encompassed by, the detailed description. The detailed description, given by way of example, but not intended to limit the invention solely to the specific embodiments described, may best be understood in conjunction with the accompanying drawings.

The invention relates to novel 5-vinylaminopyrazole derivatives, to processes for their preparation, to compositions thereof, and to their use for the control of pests (including arthropods and helminths).

The control of insects, arachnids and helminths with 1-arylpyrazole compounds has been described in several documents, for example in WO-A-87/03781, EP-A-295,117 and U.S. Pat. No. 4,695,308.

Furthermore, U.S. Pat. No. 5,629,335 discloses pesticidal 1-arylpyrazole-3-carbox-imidothioic acid esters which can have in the 5-position of the pyrazole ring a N-substituted or N,N-disubstituted amino group. Alkenyl groups are mentioned as substituents among others. Vinyl groups are not explicitly disclosed.

WO-A-99/62,886 discloses pesticidal substituted 3-thiocarbamoylpyrazoles which can have in the 5-position of the pyrazole ring a N-substituted amino group or a N,N-disubstituted amino group with selected substituents. For the N,N-disubstituted group vinyl groups are excluded as substituents.

DE-A-36 06 476 discloses 1-arylpyrazole compounds which carry in the 5-position of the pyrazole ring a N,N-disubstituted amino group. Alkenyl groups are mentioned as substituents among others. There is no explicit disclosure of vinyl groups but allyl, butenyl or pentenyl are disclosed as possible alkenyl groups.

Finally, WO-A-96/25,401 discloses pesticidal 1-arylpyrazole compounds which carry in the 5-position of the pyrazole ring an amino group which can be substituted with one or two groups. Alkenyl groups are mentioned as substituents among others. But there is no explicit disclosure of N,N-disubstituted amino groups with one substituent being a vinyl group.

However, since modern pesticides must meet a wide range of demands, for example regarding level, duration and spectrum of action, use spectrum, toxicity, combination with other active substances, combination with formulation auxiliaries or synthesis, and since the occurrence of resistances is possible, the development of such substances can never be regarded as concluded, and there is constantly a high demand for novel compounds which are advantageous over the known compounds, at least as far as some aspects are concerned.

Furthermore it has been found that 5-aminopyrazole compounds possessing a N-vinyl substitutent are compounds with an unexpected chemical stability and also with unexpected superior biological activity.

It is an object of the present invention to provide new chemical compounds which can be used in pesticidal formulation for the treatment of mammals and plants, preferably for the treatment of animals.

It is another object of the present invention to provide new pesticidal formulations which can be applied to mammals advantageously in oral form.

Another object of the invention is to provide new pesticides which may be used in lower dose than existing pesticides.

Another object of the invention is to provide new pesticides which are substantially non-emetic.

Another object of the invention is to provide new pesticides which are safer to the user and to the environment.

Another object of the invention is to provide new pesticides which provide effective pest control over an extended period of time with a single oral application.

These objects are met in whole or in part by the present invention.

The present invention provides a compound which is a 5-(vinylamino)pyrazole derivative of formula I or a pesticidical acceptable salt thereof

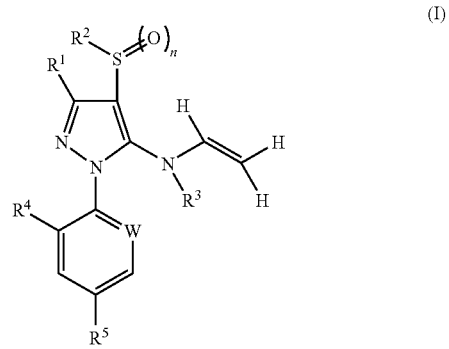

(I)

wherein

W is =N—, =CH—, =CR$^6$— or =C(NR$^7$R$^8$)—,

R$^6$ is halogen,

R$^7$ and R$^8$ are independently of one another hydrogen, alkyl, cycloalkyl, aryl, heterocyclyl, aralkyl or heterocyclylalkyl, or one of R$^7$ or R$^8$ are —CO—R$^{7a}$, —CO—O—R$^{8a}$ —SO—R$^{7a}$ or —SO$_2$R$^{7a}$, or R$^7$ and R$^8$ together with the attached N-atom form a five- to seven-membered heterocyclic ring which optionally contains an additional oxygen, sulfur or nitrogen atom in the ring or R$^7$ and R$^8$ together with the attached N-atom form an imine group —N=CR$^{7b}$R$^{8b}$ or an iminoether group —N=CR$^{7b}$(OR$^{8b}$), $R^{7a}$ and $R^{8a}$ are alkyl, cycloalkyl, aryl, heterocyclyl, aralkyl or heterocyclylalkyl, $R^{7b}$ is hydrogen, alkyl, cycloalkyl, aryl, heterocyclyl, aralkyl or heterocyclylalkyl, $R^{8b}$ is alkyl, cycloalkyl, aryl, heterocyclyl, aralkyl or heterocyclylalkyl, which groups $R^7$, $R^8$, $R^{7a}$, $R^{8a}$, $R^{7b}$ and $R^{8b}$ independently of one another are optionally substituted by one or more halogen atoms, hydroxyl, oxo, cyano, nitro, alkyl, alkoxy, alkylthio, cycloalkyl, aryl, heterocyclyl, aralkyl or heterocyclylalkyl groups or by amino, which is optionally substituted by alkyl, alkenyl, alkynyl, aryl or heteroaryl groups;

$R^1$ is cyano, halogen, alkyl, haloalkyl, or —CS—NH$_2$, $R^2$ is alkyl or cycloalkyl, which group $R^2$ is optionally substituted by one or more halogen atoms, hydroxyl, oxo, alkyl, alkoxy, alkylthio, cycloalkyl, aryl, heterocyclyl, aralkyl or heterocyclylalkyl groups;

$R^3$ is alkyl, alkenyl, alkynyl, cycloalkyl, aryl, heterocyclyl, aralkyl, heterocyclylalkyl, —CO—O—$R^9$, —CO—$R^{10}$, —SO—$R^{11}$, —SO$_2$—$R^{12}$;

$R^9$, $R^{10}$, $R^{11}$ and $R^{12}$ are alkyl, haloalkyl, alkenyl, alkynyl, cycloalkyl, aryl, heterocyclyl, aralkyl or heterocyclylalkyl, which groups $R^3$, $R^9$, $R^{10}$, $R^{11}$ and $R^{12}$ are optionally substituted by one or more halogen atoms, hydroxyl, oxo, alkyl, alkoxy, alkylthio, cycloalkyl, aryl, heterocyclyl or aralkyl groups, $R^4$ is halogen or —NR$^{13}$R$^{14}$, $R^{13}$ and $R^{14}$ are independently of one another hydrogen, alkyl, alkenyl, alkynyl, cycloalkyl, aryl, heterocyclyl, aralkyl or heterocyclylalkyl or $R^{13}$ and $R^{14}$ together with the attached N-atom form a five- to seven-membered heterocyclic ring which optionally contains an additional oxygen, sulfur or nitrogen atom in the ring, which groups $R^{13}$ and $R^{14}$ are optionally substituted by one or more halogen atoms, hydroxyl, oxo, alkyl, alkoxy, alkylthio, cycloalkyl, aryl, heterocyclyl, aralkyl or heterocyclylalkyl groups;

$R^5$ is haloalkyl, haloalkoxy, halogen or —SF$_5$, and n is an integer selected from 0, 1 or 2.

In the present specification, including the accompanying claims, the aforementioned groups have the following meanings:

The term "halogen" shall mean fluorine, chlorine, bromine or iodine. Fluorine is preferred.

The term "halo" before the name of a radical shall mean that this radical is partially or completely halogenated, that is to say, substituted by F, Cl, Br, or I, in any combination, preferably by F or Cl.

The term "alkyl" shall mean a straight-chain or branched chain saturated aliphatic hydrocarbon group. In general alkyl groups possess one to ten carbon atoms, preferably one to eight carbon atoms. Examples of alkyl groups are methyl, ethyl, propyl, isopropyl, 2-methylpropyl, 1-butyl, 2-butyl, isobutyl, tert-butyl, 2-methylbutyl, 1,1-dimethylpropyl, n-pentyl, n-hexyl, n-heptyl, 2-ethylhexyl or octyl.

The term "(C$_1$-C$_6$)-alkyl" is to be understood as meaning an unbranched or branched hydrocarbon radical having one to six carbon atoms.

Alkyl radicals preferably have 1 to 4 carbon atoms.

The term "haloalkyl" shall mean an alkyl group wherein one or more hydrogen atoms are replaced by halogen atoms, preferably by fluorine and/or chlorine. Examples for haloalkyl groups are trifluoromethyl, difluoromethyl, monofluoromethyl, 1 or 2-fluoroethyl, 2,2,2-trifluoroethyl, pentafluoroethyl, 1,1,2,2-tetrafluoroethyl, mono-, di- or trichloromethyl, 1-fluoro-2-chloro-ethyl or 2-chloroethyl.

Haloalkyl radicals preferably have 1 to 2 carbon atoms.

The term "alkoxy" shall mean a straight-chain or branched chain saturated aliphatic hydrocarbon group which is connected via an oxygen atom to another group. In general alkoxy groups possess one to ten carbon atoms, preferably one to eight carbon atoms. Examples of alkoxy groups are methoxy, ethoxy, propyloxy, isopropyloxy, 1-butyloxy, 2-butyloxy, isobutyloxy, tert-butyloxy, 2-methylbutyloxy, 1,1-dimethylpropyloxy, n-pentyloxy, n-hexyloxy, n-heptyloxy, 2-ethylhexyloxy or octyloxy.

The term "(C$_1$-C$_6$)-alkoxy" shall mean an alkoxy group whose carbon chain has the meaning given under the expression "(C$_1$-C$_6$)-alkyl".

The term "haloalkoxy" shall mean an alkoxy group wherein one or more hydrogen atoms are replaced by halogen atoms, preferably by fluorine and/or chlorine. Examples for haloalkoxy groups are trifluoromethoxy, difluoromethoxy, monofluoromethoxy, pentafluoroethoxy, 1 or 2-fluoroethoxy, 2,2,2-trifluoroethoxy, chloromethoxy, 2-chloroethoxy or 1,1,2,2-tetrafluoro-ethoxy.

The term "alkylthio" shall mean a straight-chain or branched chain saturated aliphatic hydrocarbon group which is connected via a sulfur atom to another group. In general alkylthio groups possess one to ten carbon atoms, preferably one to eight carbon atoms. Examples of alkylthio groups are methylthio, ethylthio, propylthio, isopropylthio, 1-butylthio, 2-butylthio, isobutylthio, tert-butylthio, 2-methylbutylthio, 1,1-dimethylpropylthio, n-pentylthio, n-hexylthio, n-heptylthio, 2-ethylhexylthio or octylthio.

The term "alkenyl" shall mean a straight-chain or branched chain unsaturated aliphatic hydrocarbon group possessing one or more non-conjugated double bonds. In general alkenyl groups possess one to ten carbon atoms, preferably one to eight carbon atoms. Examples of alkenyl groups are vinyl, allyl, 2-methyl-2-propenyl, 1 or 2-butenyl, pentenyl, 2-methylpentenyl, hexenyl, heptenyl or octenyl.

The term "(C$_2$-C$_6$)-alkenyl" shall mean an unbranched or branched non-cyclic carbon chain having a number of carbon atoms which corresponds to this stated range and which contains at least one double bond which can be located in any position of the respective unsaturated radical.

The term "alkynyl" shall mean a straight-chain or branched chain unsaturated aliphatic hydrocarbon group possessing one or more non-conjugated triple bonds. In general alkynyl groups possess one to ten carbon atoms, preferably one to eight carbon atoms. Examples of alkynyl groups are ethynyl, propargyl, 2-methyl-2-propynyl, 2-butynyl, 3-butynyl, pentynyl-, 2-methylpentynyl, hexynyl, heptynyl and octynyl.

The term "cycloalkyl" shall mean a monocyclic and saturated alkyl group having preferably three to seven ring carbon atoms, such as cyclopropyl, cyclobutyl, cyclopentyl, cyclohexyl, cycloheptyl, cyclooctyl or cyclodecyl; or a bicyclic and saturated alkyl group, such as norbornyl or bicyclo[2.2.2]octyl; or condensed and saturated system, such as decahydronaphthalene. Monocyclic cycloalkyl groups with five- or six-membered rings are preferred.

Cycloalkyl groups preferably are optionally substituted by halogen or alkyl.

The term "aryl" shall mean a carbocyclic aromatic group formed from ring-carbon atoms, preferably six to fourteen, especially six to twelfth ring carbon atoms. Examples for aryl groups are phenyl, naphthyl or biphenylyl, preferably phenyl.

The term "heterocyclyl" shall mean a cyclic group being fully saturated, partially unsaturated or fully unsaturated which possesses besides at least one ring carbon atom one or more ring heteroatoms selected from the group of oxygen, sulfur and nitrogen. Different ring heteroatoms are possible with the exception of two adjacent ring oxygen atoms. Heterocyclyl groups preferably contain one two or three hetero atoms in the heterocyclic ring, preferably selected from the group consisting of N, O and S. Heterocyclyl groups are preferably an aliphatic heterocyclyl radical having three to seven ring atoms or a heteroaromatic radical having five to seven ring atoms. Heteroaromatic groups can be mono-, bi- or polycyclic aromatic systems in which at least one ring contains one or more hetero atoms.

Examples of heterocyclyl groups are thiophenyl, furyl, pyrrolyl, thiazolyl, oxazolyl, imidazolyl, isothiazolyl, isoxazolyl, pyrazolyl, 1,3,4-oxadiazolyl, 1,3,4-thiadiazolyl, 1,3,4-triazolyl, 1,2,4-oxadiazolyl, 1,2,4-thiadiazolyl, 1,2,4-triazolyl, 1,2,3-triazolyl, 1,2,3,4-tetrazolyl, benzo[b]thiophenyl, benzo[b]furanyl, indolyl, benzo[c]thiophenyl, benzo[c]furanyl, isoindolyl, benzoxazolyl, benzothiazolyl, benzimidazolyl, benzisoxazolyl, benzisothiazolyl, benzopyrazolyl, benzothiadiazolyl, benzotriazolyl, dibenzofuranyl, dibenzothiophenyl, carbazolyl, pyridyl, pyrazinyl, pyrimidinyl, pyridazinyl, 1,3,5-triazinyl, 1,2,4-triazinyl, 1,2,4,5-tetrazinyl, quinolinyl, isoquinolinyl, chinoxalinyl, chinazolinyl, cinnolinyl, 1,8-naphthyridinyl, 1,5-naphthyridinyl, 1,6-naphthyridinyl, 1,7-naphthyridinyl, phthalazinyl, pyridopyrimidinyl, purinyl, pteridinyl, 4H-quinolizinyl, piperidinyl, pyrrolidinyl, oxazolinyl, tetrahydrofuranyl, tetrahydropyranyl, isoxazolidinyl, thiazolidinyl, thienyl, oxiranyl, oxetanyl, oxolanyl(=tetrahydrofuryl), oxanyl, pyrrolidyl, piperidyl, piperazinyl, dioxolanyl, oxazolinyl, isoxazolinyl, oxazolidinyl, isoxazolidinyl and morpholinyl.

The term "heteroaromatic group" is a subgroup of the term "heterocyclyl group" and encompasses the in the above list mentioned fully unsaturated aromatic heterocyclic compounds.

Heterocyclyl groups may be unsubstituted or substituted, preferably by one or more radicals, very preferably by one to three radicals selected from the group consisting of halogen, alkoxy, haloalkoxy, alkylthio, hydroxyl, amino, nitro, carboxyl, cyano, alkoxycarbonyl, alkylcarbonyl, formyl, carbamoyl, mono- and dialkylaminocarbonyl, substituted amino such as acylamino, mono- and dialkylamino, and alkylsulfinyl, haloalkylsulfinyl, alkylsulfonyl, haloalkylsulfonyl, alkyl and haloalkyl, and additionally also oxo. The oxo group can also be present at those hetero ring atoms where various oxidation numbers are possible, for example in the case of N and S.

Heterocyclyl shall preferably mean an unsaturated, partially saturated or aromatic ring system with three to six ring carbon atoms and one to four ring hetero atoms selected from the group oxygen, sulfur and nitrogen or their combinations.

Two groups together with an attached N-atom may form a five- to seven-membered heterocyclic ring which optionally contains an additional oxygen, sulfur or nitrogen atom in the ring. Examples of nitrogen-containing rings formed are given in the list of heterocyclyl groups.

The term "aralkyl" shall mean an aryl group which is connected via an alkylene group to another group. The alkylene portion is a saturated straight-chain or branched-chain hydrocarbon portion possessing in general one to six carbon atoms. Preferred aralkyl group is benzyl.

The term "heterocyclylalkyl" shall mean a heterocyclyl group which is connected via an alkylene group to another group. The alkylene portion is a saturated straight-chain or branched-chain hydrocarbon portion possessing in general one to six carbon atoms.

Preferred are compounds of formula I wherein W is =N—, =CR$^6$— or =C(NH$_2$)—, very preferred =N— and =C(halogen)-.

Very preferably W is =C(halogen)- or =N— and most preferably W is =C(halogen)-.

Preferred are compounds of formula I, wherein R$^6$ is chlorine or fluorine.

Preferred are compounds of formula I, wherein R$^1$ is cyano, halogen, alkyl, haloalkyl or —CS—NH$_2$.

R$^1$ is very preferably cyano or —CS—NH$_2$, and most preferred cyano.

Preferred are compounds of formula I, wherein R$^2$ is alkyl or haloalkyl.

R$^2$ is very preferably (C$_1$-C$_3$)-haloalkyl.

Preferably R$^3$ is —CO—O—(C$_1$-C$_6$)-alkyl, —CO—O—(C$_1$-C$_6$)-haloalkyl, —CO—O—(C$_3$-C$_6$)-alkenyl, —CO—O—(C$_2$-C$_6$)-alkynyl, —CO—O—(CH$_2$)$_m$—R$^{21}$, —(CH$_2$)$_q$—R$^{21}$, —CO—R$^{22}$, (CH$_2$)$_q$—R$^{23}$ or —SO$_2$—R$^{24}$, or (C$_1$-C$_6$)-alkyl, (C$_2$-C$_6$)-alkenyl, (C$_2$-C$_6$)-alkynyl or —CO—(C$_1$-C$_6$)-alkyl, which last 4 mentioned groups are unsubstituted or substituted by one or more R$^{25}$ radicals; or (C$_3$-C$_6$)-cycloalkyl unsubstituted or substituted by one or more radicals selected from the group consisting of halogen, (C$_1$-C$_6$)-alkyl and (C$_1$-C$_6$)-haloalkyl, wherein R$^{21}$, R$^{22}$, R$^{23}$, R$^{24}$ and R$^{25}$ are as defined below.

Preferably R$^4$ is fluorine, chlorine or bromine and very preferable chlorine.

Preferred are compounds of formula I, wherein R$^5$ is —CF$_3$, —O—CF$_3$ or —SF$_5$.

Very preferably R$^5$ is —CF$_3$ or —OCF$_3$, and most preferably R$^5$ is —CF$_3$.

Preferably R$^7$ is hydrogen, (C$_1$-C$_3$)-alkyl or (C$_1$-C$_3$)-haloalkyl.

Preferably R$^8$ is (C$_1$-C$_3$)-haloalkyl or (C$_1$-C$_3$)-alkyl optionally substituted with one or more of R$^{25}$ as defined below.

Very preferred are 5-vinylaminopyrazole derivatives of formula I, wherein

R$^1$ is —CN, (C$_1$-C$_6$)-alkyl, (C$_1$-C$_6$)-haloalkyl, halogen, or —CS—NH$_2$, R$^2$ is (C$_1$-C$_3$)-alkyl or (C$_1$-C$_3$)-haloalkyl;

W is =N—, =C(halogen)-, =CH—, =C(NR$^7$R$^8$)—;

R$^3$ is —CO—O—(C$_1$-C$_6$)-alkyl, —CO—O—(C$_1$-C$_6$)-haloalkyl, —CO—O—(C$_3$-C$_6$)-alkenyl, —CO—O—(C$_2$-C$_6$)-alkynyl, —CO—O—(CH$_2$)$_m$—R$^{21}$, —(CH$_2$)$_q$—R$^{21}$, —CO—R$^{22}$, —(CH$_2$)$_q$—R$^{23}$ or —SO$_2$—R$^{24}$; or R$^3$ is (C$_1$-C$_6$)-alkyl, (C$_2$-C$_6$)-alkenyl, (C$_2$-C$_6$)-alkynyl or —CO—(C$_1$-C$_6$)-alkyl, which last 4 mentioned groups are unsubstituted or substituted by one or more R$^{25}$ radicals; or R$^3$ is (C$_3$-C$_6$)-cycloalkyl unsubstituted or substituted by one or more radicals selected from the group consisting of halogen, (C$_1$-C$_6$)-alkyl and (C$_1$-C$_6$)-haloalkyl;

R$^4$ is halogen or —NR$^{13}$R$^{14}$,

R$^5$ is —CF$_3$, —O—CF$_3$, or —SF$_5$,

R$^7$ is hydrogen, (C$_1$-C$_6$)-alkyl, (C$_1$-C$_6$)-haloalkyl, (C$_2$-C$_6$)-alkenyl, (C$_2$-C$_6$)-alkynyl or —(CH$_2$)$_q$—R$^{21}$, R$^8$ is (C$_1$-C$_4$)-haloalkyl or (C$_1$-C$_4$)-alkyl which is optionally substituted with one or more of R$^{25}$, or R$^7$ and R$^8$ together with the attached N atom form a five- to seven-membered saturated or unsaturated ring which optionally contains an additional hetero atom in the ring which is selected from O, S and N, the ring being unsubstituted or substituted by one or more radicals selected from the group consisting of halogen, (C$_1$-C$_6$)-alkyl, (C$_1$-C$_6$)-haloalkyl, (C$_1$-C$_6$)-alkoxy and oxo;

R$^{21}$ is phenyl unsubstituted or substituted by one or more radicals selected from the group consisting of halogen, (C$_1$-C$_6$)-alkyl, (C$_1$-C$_6$)-haloalkyl, (C$_1$-C$_6$)-alkoxy, (C$_1$-C$_6$)-haloalkoxy, —CN, —NO$_2$, —OH, —S(O)$_p$R$^{26}$ and —NR$^{27}$R$^{28}$;

$R^{22}$ is hydrogen, $(C_1-C_6)$-alkyl, $(C_3-C_6)$-cycloalkyl, $(C_3-C_6)$-cycloalkyl-$(C_1-C_4)$-alkyl, —$(CH_2)_q$—$R^{21}$ or —$(CH_2)_q$—$R^{23}$, which groups $(C_1-C_6)$-alkyl, $(C_3-C_6)$-cycloalkyl or $(C_3-C_6)$-cycloalkyl-$(C_1-C_4)$-alkyl are optionally substituted by one or more $R^{25}$ radicals, $R^{23}$ is heterocyclyl unsubstituted or substituted by one or more radicals selected from the group consisting of halogen, $(C_1-C_4)$-alkyl, $(C_1-C_4)$-haloalkyl, $(C_1-C_4)$-alkoxy, $(C_1-C_4)$-haloalkoxy, —$NO_2$, —CN, —CO—O—$(C_1-C_6)$-alkyl, —$S(O)_p$—$R^{26}$, —OH and oxo, $R^{24}$ is $(C_3-C_6)$-cycloalkyl, $(C_2-C_6)$-alkenyl, $(C_2-C_6)$-haloalkenyl, $(C_2-C_6)$-alkynyl, $(C_2-C_6)$-haloalkynyl, —$(CH_2)_q$—$R^{21}$ or —$(CH_2)_q$—$R^{23}$; or $R^{24}$ is $(C_1-C_6)$-alkyl unsubstituted or substituted by one or more radicals selected from the group consisting of $R^{29}$, $R^{25}$ and $R^{29}$ independently of one another are halogen, $(C_1-C_6)$-alkyl, $(C_1-C_6)$-alkoxy, $(C_1-C_6)$-haloalkoxy, $(C_3-C_6)$-alkenyloxy, $(C_3-C_6)$-haloalkenyloxy, $(C_3-C_6)$-alkynyloxy, $(C_3-C_6)$-haloalkynyloxy, $(C_3-C_7)$-cycloalkyl, —$S(O)_p$—$R^{30}$, —CN, —$NO_2$, —OH, —CO—$R^{26}$, —$NR^{22}R^{27}$, —$NR^{22}$—$COR^{27}$, —$NR^{22}$—$SO_2$—$R^{30}$, —CO—$NR^{22}R^{27}$, —$SO_2$—$NR^{22}R^{27}$, —O—$(CH_2)_q$—$R^{21}$, —O—$(CH_2)_q$—$R^{23}$, —O—$NR^{22}R^{31}$ or —CO—O—$R^{26}$;

$R^{26}$ is $(C_1-C_6)$-alkyl or $(C_1-C_6)$-haloalkyl, $R^{27}$ and $R^{28}$ are independently of one another hydrogen, $(C_1-C_6)$-haloalkyl, $(C_3-C_6)$-alkenyl, $(C_3-C_6)$-haloalkenyl, $(C_3-C_6)$-alkynyl, $(C_3-C_6)$-cycloalkyl, $(C_3-C_6)$-cycloalkyl-$(C_1-C_6)$-alkyl or $(C_1-C_6)$-alkyl optionally substituted with one or more of $R^{29}$, or $R^{27}$ and $R^{28}$ together with the attached N atom form a five- or six-membered saturated or unsaturated ring which optionally contains an additional hetero atom in the ring which is selected from O, S and N, the ring being unsubstituted or substituted by one or more radicals selected from the group consisting of halogen, $(C_1-C_6)$-alkyl, $(C_1-C_6)$-haloalkyl, $(C_1-C_6)$-alkoxy, $(C_1-C_6)$-alkylthio and oxo, $R^{30}$ is $(C_1-C_6)$-alkyl, $(C_1-C_6)$-haloalkyl, $(C_3-C_6)$-alkenyl, $(C_3-C_6)$-haloalkenyl, $(C_3-C_6)$-alkynyl, $(C_3-C_6)$-cycloalkyl or —$(CH_2)_q$—$R^{21}$, $R^{31}$ is $(C_1-C_6)$-alkyl, $(C_1-C_6)$-haloalkyl, $(C_3-C_6)$-cycloalkyl, $(C_3-C_6)$-cycloalkyl-$(C_1-C_4)$-alkyl, —$(CH_2)_q$—$R^{21}$ or —$(CH_2)_q$—$R^{23}$, m and q can independently be 0 or 1, n and p can independently be 0, 1 or 2, and each heterocyclyl in the above-mentioned radicals is independently a heterocyclic radical having 3 to 7 ring atoms and 1, 2 or 3 hetero atoms in the ring selected from the group consisting of nitrogen, oxygen and sulfur;

or a pesticidally acceptable salt thereof.

The compounds of formula I or their pesticidally acceptable salts possess valuable pesticidal properties.

By the term "pesticidally acceptable salts" is meant salts the anions or cations of which are known and accepted in the art for the formation of salts for pesticidal use.

Suitable salts with bases, e.g. formed by compounds of formula I containing an acidic groups, such as a carboxylic acid group, include alkali metal (e.g. sodium and potassium), alkaline earth metal (e.g. calcium and magnesium), ammonium and amine (e.g. diethanolamine, triethanolamine, octylamine, morpholine and dioctylmethylamine) salts. Suitable acid addition salts, e.g. formed by compounds of formula I containing a basic group, such as an amino group, include salts with inorganic acids, for example hydrochlorides, sulphates, phosphates and nitrates and salts with organic acids for example acetic acid.

The term "pest" shall mean arthropod pests (including insects and arachnids), and helminths (including nematodes).

In the following preferred definitions it is generally to be understood that where symbols are not specifically defined they are to be as previously defined in the description.

A preferred class of compounds of formula I for use in the invention are those in which:

$R^1$ is —CN, $R^2$ is $(C_1-C_3)$-haloalkyl,

W is =C(halogen)-, $R^3$ is $(C_1-C_6)$-alkyl optionally substituted by one or more $R^{25}$ radicals as defined above, $R^4$ is halogen or —$NR^{13}R^{14}$, $R^5$ is —$CF_3$;

$R^{13}$ is hydrogen or $(C_1-C_3)$-alkyl; and $R^{14}$ is $(C_1-C_3)$-haloalkyl or $(C_1-C_3)$-alkyl optionally substituted with one or more of $R^{25}$ as defined above.

A more preferred class of compounds of formula I for use in the invention are those in which:

$R^1$ is —CN, $R^2$ is —$CF_3$,

W is =C(Cl)—, $R^3$ is methyl, $R^4$ is —Cl, and $R^5$ is —$CF_3$.

The compounds of general formula I can be prepared by the application or adaptation of known methods (i.e. methods heretofore used or described in the chemical literature).

In the following description of processes when symbols appearing in formulae are not specifically defined, it is understood that they are "as defined above" in accordance with the first definition of each symbol in the specification.

According to a further feature of the invention compounds of formula I may be prepared by the reaction of a compound of formula II:

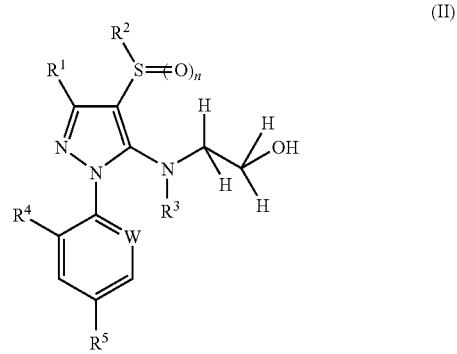

(II)

wherein $R^1$, $R^2$, $R^3$, $R^4$, $R^5$, W and index n are as defined above with chromiun oxide/pyridine in a halogenated solvent at room temperature or elevated temperature.

In an alternative procedure compounds of formula I may be also be prepared by the treatment of compound of formula III with organic or inorganic base in an aprotic organic solvent like THF, ether, acetonitrile, or in a halogenated solvent with temperature ranging from 0° C. to elevated temperature, for example to the boiling point of the organic solvent used. Reaction temperatures are, for example, in the range between 0° C. and 150° C.

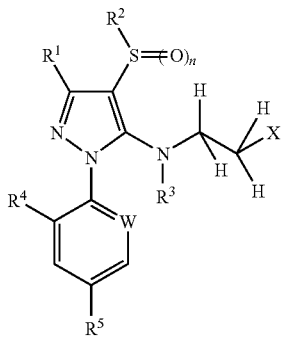

(III)

In formula III X is a halogen atom or another leaving group, for example mesylate or tosylate, and $R^1$, $R^2$, $R^3$, $R^4$, $R^5$, W and n are as defined above.

The base used is generally an alkali metal carbonate, such as potassium carbonate or sodium carbonate, or an organic base, such as a tertiary amine, for example triethylamine or ethyldiisopropylamine, or pyridine, or 1,8-diazabicyclo[5.4.0]undec-7-en (DBU).

According to a further feature of the invention compounds of formula I wherein $R^1$ is —CS—$NH_2$, and the other groups are as defined above, may be prepared by the reaction of the corresponding compound of formula I wherein $R^1$ is CN, with a bis-(trialkylsilyl)-sulfide, preferably bis-(trimethylsilyl)-sulfide, in the presence of a base, generally an alkali metal alkoxide, such as sodium methoxide, and in an aprotic organic solvent, such as N,N-dimethylformamide, at a temperature of from 0° C. to 60° C. The procedure is generally described by Lin, Ku and Shiao in Synthesis 1219 (1992).

According to a further feature of the invention compounds of formula I wherein $R^1$ is —CN, n is 1 or 2, and the other groups are as defined above, may be prepared by oxidising a corresponding compound of formula I in which n is 0 or 1. The oxidation is generally performed using a peracid such as 3-chloroperbenzoic acid in an organic solvent, such as dichloromethane or 1,2-dichloroethane, at a temperature of from 0° C. to the reflux temperature of the solvent.

Intermediates of formula II may be prepared by the reaction of a compound of formula IV:

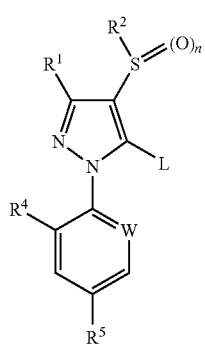

(IV)

wherein $R^1$, $R^2$, $R^4$, $R^5$, W and index n are as defined above and L is a leaving group, generally halogen and preferably Br, with a compound of formula V:

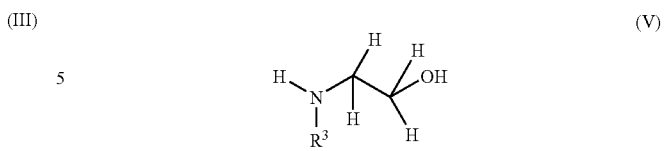

(V)

wherein $R^3$ is as defined above. The reaction is generally performed in the presence of a base, preferably an alkali metal phosphate, such as potassium phosphate, in an inert solvent such as acetonitrile, at a temperature of from 20° C. to 100° C.

Intermediate III can be prepared by the reaction of intermediate II with the corresponding substituted sulfonyl chloride in the presence of organic or inorganic bases in organic solvents, such as acetonitrile, tetrahydrofuran, diethyl ether or dimethyl formamide. The reaction temperature can proceed from −10° C. to the refluxing solvent temperature.

The corresponding resulting intermediate III with X being mesylate or tosylate can be reacted further with metal halide (e.g. NaI or NaBr) in the solvent, such as acetone at room temperature to elevated temperature to provide the resulting intermediate III where X is a halogen.

Collections of compounds of the formula I which can be synthesized by the above mentioned process may also be prepared in a parallel manner, and this may be effected manually or in a semiautomated or fully automated manner. In this case, it is possible, for example, to automate the procedure of the reaction, work-up or purification of the products or of the intermediates. In total, this is to be understood as meaning a procedure as is described, for example, by S. H. DeWitt in "Annual Reports in Combinatorial Chemistry and Molecular Diversity: Automated Synthesis", Volume 1, Verlag Escom 1997, pages 69 to 77.

A series of commercially available apparatuses as are offered by, for example, Stem Corporation, Woodrolfe Road, Tollesbury, Essex, CM9 8SE, England or H+P Labortechnik GmbH, Bruckmannring 28, 85764 Oberschleißheim, Germany or Radleys, Shirehill, Saffron Walden, Essex, England, may be used for the parallel procedure of the reaction and work-up. For the parallel purification of compounds of the formula I, or of intermediates obtained during the preparation, use may be made, inter alia, of chromatography apparatuses, for example those by ISCO, Inc., 4700 Superior Street, Lincoln, Nebr. 68504, USA.

The apparatuses mentioned lead to a modular procedure in which the individual process steps are automated, but manual operations must be performed between the process steps. This can be prevented by employing semi-integrated or fully integrated automation systems where the automation modules in question are operated by, for example, robots. Such automation systems can be obtained, for example, from Zymark Corporation, Zymark Center, Hopkinton, Mass. 01748, USA.

In addition to what has been described here, compounds of the formula I may be prepared in part or fully by solid-phase-supported methods. For this purpose, individual intermediate steps or all intermediate steps of the synthesis or of a synthesis adapted to suit the procedure in question are bound to a synthetic resin. Solid-phase-supported synthesis methods are described extensively in the specialist literature, for example Barry A. Bunin in "The Combinatorial Index", Academic Press, 1998.

The use of solid-phase-supported synthesis methods permits a series of protocols which are known from the literature and which, in turn, can be performed manually or in an automated manner. For example, the "tea-bag method" (Houghten, U.S. Pat. No. 4,631,211; Houghten et al., Proc. Natl. Acad. Sci, 1985, 82, 5131-5135), in which products by IRORI, 11149 North Torrey Pines Road, La Jolla, Calif. 92037, USA, are employed, may be semiautomated. The automation of solid-phase-supported parallel syntheses is performed successfully, for example, by apparatuses by Argonaut Technologies, Inc., 887 Industrial Road, San Carlos, Calif. 94070, USA or MultiSynTech GmbH, Wullener Feld 4, 58454 Witten, Germany.

The preparation of the processes described herein yields compounds of the formula I in the form of substance collections which are termed libraries. The present invention also relates to libraries which comprise at least two compounds of the formula I.

The compounds of formula III, wherein X is halogen, are novel and as such form a further part of the invention. Those compounds of formula II, in particular where $R^1$ is —CN and X is halogen also possess very useful pesticidal activity, for example in the systemic control of *Ctenocephalides felis* (cat flea).

A preferred class of compounds of formula III are those in which X is iodine.

A very preferred class of compounds of formula III are those in which:
$R^1$ is —CN,
$R^2$ and $R^5$ are each —$CF_3$,
$R^4$ is —Cl, and
X is bromine or very preferred iodine.

The following non-limiting Examples illustrate the preparation of the compounds of formula I.

CHEMICAL EXAMPLES

NMR spectra were run in deuterochloroform unless stated otherwise. In the Examples which follow, quantities (also percentages) are weight based, unless stated otherwise. Ratios of solvents are volume based.

Example 1

1-[2,6-dichloro-4-(trifluoromethyl)phenyl]-5-[methyl (vinyl)amino]-4-[(trifluoromethyl)sulfonyl]-1H-pyrazole-3-carbonitrile To a solution of pyridine (0.186 g, 0.23 mmol) in dichloromethane (10 mL) was slowly added chromium (VI) oxide (0.119 g, 0.12 mmol) at room temperature under nitrogen. The resulting mixture was stirred at room temperature for 15 minutes before 1-[2,6-dichloro-4-(trifluoromethyl)phenyl]-5-[(2-hydroxy-ethyl)(methyl)amino]-4-[(trifluoromethyl) sulfonyl]-1H-pyrazole-3-carbonitrile (0.200 g, 0.4 mmol) was introduced. The reaction mixture was allowed to stirr at room temperature for two additional hours. It was then concentrated to dryness and then diluted with diethyl ether. The mixture was then filtered through silica gel and then concentrated to afford a pale oil (0.04 g, 0.1 mmol). 19F NMR: −64.37, −80.74.

The following Intermediate Examples illustrate the preparation of intermediates used in the synthesis of the above Examples.

Intermediate Example 1

1-[2,6-dichloro-4-(trifluoromethyl)phenyl]-5-[(2-hydroxyethyl)(methyl)amino]-4-[(trifluoromethyl) sulfonyl]-1H-pyrazole-3-carbonitrile Finely powdered potassium carbonate (7.29 g, 52.2 mmol) was added to a solution of 5-bromo-1-(2,6-dichloro-4-trifluoromethylphenyl)-3-cyano-4-trifluoromethylsulphonylpyrazole (10.00 g, 19.3 mmol) in dry N,N-dimethylformamide (85 ml) and stirred for 1 hour at 20° C. 2-(Methylamino) ethanol (3.11 ml, 38.7 mmol) was then added and stirring continued for 2 hours at 20° C. The resulting mixture was poured into saturated ammonium chloride solution, extracted with ethyl acetate, and the organic layer washed with water and brine, dried (sodium sulfate), evaporated and purified by column chromatography eluting with hexane and ethyl acetate (2:1) to give 1-(2,6-dichloro-4-trifluoromethylphenyl)-3-cyano-5-[N-(2-hydroxyethyl)-N-methylamino]-4-trifluoromethylsulfonylpyrazole as a fine white powder (5.65 g, yield 57%), 19F-NMR: −63.7, −78.4.

Intermediate Example 2

1-[2,6-dichloro-4-(trifluoromethyl)phenyl]-5-[(2-iodoethy)(methyl)amino]-4-[(trifluoromethyl)sulfonyl]-1H-pyrazole-3-carbonitrile To the solution of 1-[2,6-dichloro-4-(trifluoromethyl)phenyl]-5-[(hydroxy-ethyl)(methyl)amino]-4-[(trifluoromethyl) sulfonyl]-1H-pyrazole-3-carbonitrile (0.206 g, 0.4 mmol) in tetrahydrofuran (15 mL) was added N,N-diisopropyl-ethylamine (0.068 g, 0.5 mmol) and 4-dimethylaminopyridine (0.012 g, 0.1 mmol). The resulting solution was stirred at room temperature for 10 minutes and then was added methanesulfonyl chloride (0.052 g, 0.4 mmol). After stirring at 45 C for 1.5 hour, the resulting mixture was heated to reflux for 1.75 hours. It was then cooled and was added methanesulfonyl fluoride (31.2 uL, 0.5 mmol) and N,N-diisopropylethylamine (0.068 g, 0.5 mmol). The resulting mixture was then heated again to reflux for one hour. It was then cooled and poured into saturated ammonium chloride and ethyl acetate. The layers were separated and the organic layer was washed with water, brine, dried $Na_2SO_4$), and concentrated to afford a clear oil (0.25 g) which was used directly in the procedure below.

To the above clear oil in tetrahydrofuran (15 mL) was added sodium iodide (0.064 g, 0.4 mmol). The resulting mixture was heated to reflux for five hours and then cooled. It was then poured into saturated ammonium chloride and ethyl acetate. The layers were separated and the organic layer was washed with water, brine, dried ($Na_2SO_4$), and concentrated to afford an orange-colored oil. Upon chromatographic purification via silica gel column eluting with heptane/ethyl acetate (9/1 to 4/1), an orange-colored oil (27.6 mg, 0.044 mmol) was obtained. 19FNMR: −63.76, −78.52.

The following preferred compounds shown in Tables 1 to 5 also form part of the present invention, and were or may be prepared in accordance with, or analogously to, the above-mentioned Examples 1 or the above-described general methods. Where subscripts are omitted they are intended, for example CH2 means $CH_2$.

In the Tables Me means methyl, Et means ethyl, Pr means n-propyl, i-Pr means isopropyl, t-Bu means tertiary butyl, OMe means methoxy, OEt means ethoxy, Ph means phenyl, CO-(4-ClPh) means 4-chlorobenzoyl, and COO—CH2-(4-OMePh) means (4-methoxybenzyloxycarbonyl.

$^{19}$F-NMR spectra shift values are given in ppm.

Compound numbers are given for reference purposes only.

TABLE 1

Compounds of formula I in which the substituents have the following meanings: $R^1$ is —CN; $R^2$ is —$CF_3$; $R^4$ is —Cl; W is =C(Cl)—

| Compound No. | $R^3$ | $R^5$ | n | $^{19}$FNMR or m.p. |
|---|---|---|---|---|
| 1-1 | Me | CF3 | 2 | −63.76, −78.52 |
| 1-2 | Me | CF3 | 1 | |
| 1-3 | Me | CF3 | 0 | |
| 1-4 | Et | CF3 | 2 | |
| 1-5 | Et | CF3 | 1 | |
| 1-6 | Et | CF3 | 0 | |
| 1-7 | Me | OCF3 | 2 | |
| 1-8 | Me | OCF3 | 1 | |
| 1-9 | Me | OCF3 | 0 | |
| 1-10 | CO2Et | CF3 | 2 | |
| 1-11 | CO2Et | CF3 | 1 | |
| 1-12 | CO2Et | CF3 | 0 | |
| 1-13 | COMe | CF3 | 2 | |
| 1-14 | COMe | CF3 | 1 | |
| 1-15 | COMe | CF3 | 0 | |
| 1-16 | c-Pr | CF3 | 2 | |
| 1-17 | c-Pr | CF3 | 1 | |
| 1-18 | c-Pr | CF3 | 0 | |
| 1-19 | CH2Ph | CF3 | 2 | |
| 1-20 | CH2Ph | CF3 | 1 | |
| 1-21 | CH2Ph | CF3 | 0 | |
| 1-22 | SO2Ph | CF3 | 2 | |
| 1-23 | SO2Ph | CF3 | 1 | |
| 1-24 | SO2Ph | CF3 | 0 | |
| 1-25 | allyl | CF3 | 2 | |
| 1-26 | allyl | CF3 | 1 | |
| 1-27 | allyl | CF3 | 0 | |
| 1-28 | c-Pr | OCF3 | 2 | |
| 1-29 | c-Pr | OCF3 | 1 | |
| 1-30 | c-Pr | OCF3 | 0 | |

TABLE 2

Compounds of formula (I) in which the substituents have the following meanings: $R^1$ is —CN; $R^2$ is —$CCl_2F$; $R^4$ is —Cl; W is =C(Cl)—

| Compound No. | $R^3$ | $R^5$ | n | $^{19}$FNMR or m.p. |
|---|---|---|---|---|
| 2-1 | Me | CF3 | 2 | |
| 2-2 | Me | CF3 | 1 | |
| 2-3 | Me | CF3 | 0 | |
| 2-4 | Et | CF3 | 2 | |
| 2-5 | Et | CF3 | 1 | |
| 2-6 | Et | CF3 | 0 | |
| 2-7 | Me | OCF3 | 2 | |
| 2-8 | Me | OCF3 | 1 | |
| 2-9 | Me | OCF3 | 0 | |
| 2-10 | CO2Et | CF3 | 2 | |
| 2-11 | CO2Et | CF3 | 1 | |
| 2-12 | CO2Et | CF3 | 0 | |
| 2-13 | COMe | CF3 | 2 | |
| 2-14 | COMe | CF3 | 1 | |
| 2-15 | COMe | CF3 | 0 | |
| 2-16 | c-Pr | CF3 | 2 | |
| 2-17 | c-Pr | CF3 | 1 | |
| 2-18 | c-Pr | CF3 | 0 | |
| 2-19 | CH2Ph | CF3 | 2 | |
| 2-20 | CH2Ph | CF3 | 1 | |
| 2-21 | CH2Ph | CF3 | 0 | |
| 2-22 | SO2Ph | CF3 | 2 | |
| 2-23 | SO2Ph | CF3 | 1 | |
| 2-24 | SO2Ph | CF3 | 0 | |
| 2-25 | allyl | CF3 | 2 | |
| 2-26 | allyl | CF3 | 1 | |
| 2-27 | allyl | CF3 | 0 | |
| 2-28 | c-Pr | OCF3 | 2 | |
| 2-29 | c-Pr | OCF3 | 1 | |
| 2-30 | c-Pr | OCF3 | 0 | |

TABLE 3

Compounds of formula I in which the substituents have the following meanings: $R^1$ is —CN; $R^2$ is —$CF_3$; $R^4$ is —Cl; W is =C(NHEt)-

| Compound No. | $R^3$ | $R^5$ | n | $^{19}$NMR or m.p. |
|---|---|---|---|---|
| 3-1 | Me | CF3 | 2 | |
| 3-2 | Me | CF3 | 1 | |
| 3-3 | Me | CF3 | 0 | |
| 3-4 | Et | CF3 | 2 | |
| 3-5 | Et | CF3 | 1 | |
| 3-6 | Et | CF3 | 0 | |
| 3-7 | Me | OCF3 | 2 | |
| 3-8 | Me | OCF3 | 1 | |
| 3-9 | Me | OCF3 | 0 | |
| 3-10 | CO2Et | CF3 | 2 | |
| 3-11 | CO2Et | CF3 | 1 | |
| 3-12 | CO2Et | CF3 | 0 | |
| 3-13 | COMe | CF3 | 2 | |
| 3-14 | COMe | CF3 | 1 | |
| 3-15 | COMe | CF3 | 0 | |
| 3-16 | c-Pr | CF3 | 2 | |
| 3-17 | c-Pr | CF3 | 1 | |
| 3-18 | c-Pr | CF3 | 0 | |
| 3-19 | CH2Ph | CF3 | 2 | |
| 3-20 | CH2Ph | CF3 | 1 | |
| 3-21 | CH2Ph | CF3 | 0 | |
| 3-22 | SO2Ph | CF3 | 2 | |
| 3-23 | SO2Ph | CF3 | 1 | |
| 3-24 | SO2Ph | CF3 | 0 | |
| 3-25 | allyl | CF3 | 2 | |
| 3-26 | allyl | CF3 | 1 | |
| 3-27 | allyl | CF3 | 0 | |
| 3-28 | c-Pr | OCF3 | 2 | |
| 3-29 | c-Pr | OCF3 | 1 | |
| 3-30 | c-Pr | OCF3 | 0 | |

TABLE 4

Compounds of formula I in which the substituents have the following meanings: $R^1$ is —CN; $R^2$ is —$CF_3$; $R^4$ is —Cl; W is =N—

| Compound No. | $R^3$ | $R^5$ | n | $^{19}$FNMR or m.p. |
|---|---|---|---|---|
| 4-1 | Me | CF3 | 2 | |
| 4-2 | Me | CF3 | 1 | |
| 4-3 | Me | CF3 | 0 | |
| 4-4 | Et | CF3 | 2 | |
| 4-5 | Et | CF3 | 1 | |
| 4-6 | Et | CF3 | 0 | |
| 4-7 | Me | OCF3 | 2 | |
| 4-8 | Me | OCF3 | 1 | |
| 4-9 | Me | OCF3 | 0 | |
| 4-10 | CO2Et | CF3 | 2 | |
| 4-11 | CO2Et | CF3 | 1 | |
| 4-12 | CO2Et | CF3 | 0 | |
| 4-13 | COMe | CF3 | 2 | |
| 4-14 | COMe | CF3 | 1 | |
| 4-15 | COMe | CF3 | 0 | |
| 4-16 | c-Pr | CF3 | 2 | |
| 4-17 | c-Pr | CF3 | 1 | |
| 4-18 | c-Pr | CF3 | 0 | |
| 4-19 | CH2Ph | CF3 | 2 | |
| 4-20 | CH2Ph | CF3 | 1 | |
| 4-21 | CH2Ph | CF3 | 0 | |
| 4-22 | SO2Ph | CF3 | 2 | |
| 4-23 | SO2Ph | CF3 | 1 | |
| 4-24 | SO2Ph | CF3 | 0 | |
| 4-25 | allyl | CF3 | 2 | |
| 4-26 | allyl | CF3 | 1 | |
| 4-27 | allyl | CF3 | 0 | |
| 4-28 | c-Pr | OCF3 | 2 | |
| 4-29 | c-Pr | OCF3 | 1 | |
| 4-30 | c-Pr | OCF3 | 0 | |

TABLE 5

Compounds of formula I in which the substituents have the following meanings: $R^1$ is —CN; $R^2$ is —CF$_3$; $R^4$ is —Cl; W is =C(N(Me)$_2$)-

| Compound No. | R$^3$ | R$^5$ | n | $^{19}$FNMR or m.p. |
|---|---|---|---|---|
| 5-1 | Me | CF3 | 2 | |
| 5-2 | Me | CF3 | 1 | |
| 5-3 | Me | CF3 | 0 | |
| 5-4 | Et | CF3 | 2 | |
| 5-5 | Et | CF3 | 1 | |
| 5-6 | Et | CF3 | 0 | |
| 5-7 | Me | OCF3 | 2 | |
| 5-8 | Me | OCF3 | 1 | |
| 5-9 | Me | OCF3 | 0 | |
| 5-10 | CO2Et | CF3 | 2 | |
| 5-11 | CO2Et | CF3 | 1 | |
| 5-12 | CO2Et | CF3 | 0 | |
| 5-13 | COMe | CF3 | 2 | |
| 5-14 | COMe | CF3 | 1 | |
| 5-15 | COMe | CF3 | 0 | |
| 5-16 | c-Pr | CF3 | 2 | |
| 5-17 | c-Pr | CF3 | 1 | |
| 5-18 | c-Pr | CF3 | 0 | |
| 5-19 | CH2Ph | CF3 | 2 | |
| 5-20 | CH2Ph | CF3 | 1 | |
| 5-21 | CH2Ph | CF3 | 0 | |
| 5-22 | SO2Ph | CF3 | 2 | |
| 5-23 | SO2Ph | CF3 | 1 | |
| 5-24 | SO2Ph | CF3 | 0 | |
| 5-25 | allyl | CF3 | 2 | |
| 5-26 | allyl | CF3 | 1 | |
| 5-27 | allyl | CF3 | 0 | |
| 5-28 | c-Pr | OCF3 | 2 | |
| 5-29 | c-Pr | OCF3 | 1 | |
| 5-30 | c-Pr | OCF3 | 0 | |

According to a further feature of the present invention there is provided a method for the control of pests at a locus which comprises applying thereto an effective amount of a compound of formula I or a salt thereof. For this purpose, the said compound is normally used in the form of a pesticidal composition (i.e. in association with compatible diluents or carriers and/or surface active agents suitable for use in pesticidal compositions), for example as hereinafter described.

The term "compound of the invention" as used hereinafter embraces a 5-(1-vinyl)aminopyrazole of formula I as defined above and a pesticidal acceptable salt thereof and/or a compound of formula III as defined above and a pesticidal acceptable salt thereof.

One aspect of the present invention as defined above is a method for the control of pests at a locus. The locus includes, for example, the pest itself, the place (plant, field, forest, orchard, waterway, soil, plant product, or the like) where the pest resides or feeds, or a place susceptible to future infestation by the pest. The compound of the invention may therefore be applied directly to the pest, to the place where the pest resides or feeds, or to the place susceptible to future infestation by the pest.

As is evident from the foregoing pesticidal uses, the present invention provides pesticidally active compounds and methods of use of said compounds for the control of a number of pest species which includes: arthropods, especially insects or mites, or plant nematodes.

The compound of the invention may thus be advantageously employed in practical uses, for example, in agricultural or horticultural crops, in forestry, in veterinary medicine or livestock husbandry, or in public health.

The compounds of the invention may be used for example in the following applications and on the following pests:

For the control of soil insects, such as corn rootworm, termites (especially for protection of structures), root maggots, wireworms, root weevils, stalkborers, cutworms, root aphids, or grubs.

They may also be used to provide activity against plant pathogenic nematodes, such as root-knot, cyst, dagger, lesion, or stem or bulb nematodes, or against mites.

For the control of soil pests, for example corn rootworm, the compounds are advantageously applied to or incorporated at an effective rate into the soil in which crops are planted or to be planted or to the seeds or growing plant roots.

In the area of public health, the compounds are especially useful in the control of many insects, especially filth flies or other Dipteran pests, such as houseflies, stableflies, soldierflies, hornflies, deerflies, horseflies, midges, punkies, blackflies, or mosquitoes.

In the protection of stored products, for example cereals, including grain or flour, groundnuts, animal feedstuffs, timber or household goods, e.g. carpets and textiles, compounds of the invention are useful against attack by arthropods, more especially beetles, including weevils, moths or mites, for example *Ephestia* spp. (flour moths), *Anthrenus* spp. (carpet beetles), *Tribolium* spp. (flour beetles), *Sitophilus* spp. (grain weevils) or *Acarus* spp. (mites). In the control of cockroaches, ants or termites or similar arthropod pests in infested domestic or industrial premises or in the control of mosquito larvae in waterways, wells, reservoirs or other running or standing water. For the treatment of foundations, structures or soil in the prevention of the attack on building by termites, for example, *Reticulitermes* spp., *Heterotermes* spp., *Coptotermes* spp.

In agriculture against adults, larvae and eggs of *Lepidoptera* (butterflies and moths), e.g. *Heliothis* spp. such as *Heliothis virescens* (tobacco budworm), *Heliothis armigera* and *Heliothis zea*. Against adults and larvae of *Coleoptera* (beetles) e.g. *Anthonomus* spp. e.g. *grandis* (cotton boll weevil), *Leptinotarsa decemlineata* (Colorado potato beetle), *Diabrotica* spp. (corn rootworms). Against Heteroptera (*Hemiptera* and *Homoptera*) e.g. *Psylla* spp., *Bemisia* spp., *Trialeurodes* spp., *Aphis* spp., *Myzus* spp., *Megoura viciae*, *Phylloxera* spp., *Nephotettix* spp. (rice leaf hoppers), *Nilaparvata* spp.

Against *Diptera* e.g. *Musca* spp. Against Thysanoptera such as *Thrips tabaci*. Against Orthoptera such as *Locusta* and *Schistocerca* spp., (locusts and crickets) e.g. *Gryllus* spp., and *Acheta* spp. for example, *Blatta orientalis*, *Periplaneta americana*, *Blatella germanica*, *Locusta migratoria migratorioides*, and *Schistocerca gregaria*. Against Collembola e.g. *Periplaneta* spp. and *Blatella* spp. (roaches).

Against arthropods of agricultural significance such as Acari (mites) e.g. *Tetranychus* spp., and *Panonychus* spp.

Against nematodes which attack plants or trees of importance to agriculture, forestry or horticulture either directly or by spreading bacterial, viral, mycoplasma or fungal diseases of the plants. For example root-knot nematodes such as *Meloidogyne* spp. (e.g. *M. incognita*).

In the field of veterinary medicine or livestock husbandry or in the maintenance of public health against arthropods which are parasitic internally or externally upon vertebrates, particularly warm-blooded vertebrates, for example domestic animals, e.g. cattle, sheep, goats, equines, swine, poultry, dogs or cats, for example Acarina, including ticks (e.g. soft-bodied ticks including *Argasidae* spp. e.g. *Argas* spp. and *Ornithodorus* spp. (e.g. *Ornithodorus moubata*); hard-bodied ticks including *Ixodidae* spp., e.g. *Boophilus* spp. e.g. *Boophilus microplus*, *Rhipicephalus* spp. e.g. *Rhipicephalus appendiculatus* and *Rhipicephalus sanguineus*; mites (e.g.

*Damalinia* spp.); fleas (e.g. *Ctenocephalides* spp. e.g. *Ctenocephalides felis* (cat flea) and *Ctenocephalides canis* (dog flea)); lice e.g. *Menopon* spp.; *Diptera* (e.g. *Aedes* spp., *Anopheles* spp., *Musca* spp., *Hypoderma* spp.); *Hemiptera; Dictyoptera* (e.g. *Periplaneta* spp., *Blatella* spp.); *Hymenoptera*; for example against infections of the gastro-intestinal tract caused by parasitic nematode worms, for example members of the family Trichostrongylidae.

In a preferred aspect of the invention the compounds of formula I or salts or compositions thereof are used for the control of parasites of animals. Preferably the animal to be treated is a domestic companion animal such as a dog or a cat.

In a further aspect of the invention the compounds of formula I or salts or compositions thereof are used for the preparation of a veterinary medicament.

A further feature of the invention thus relates to the use of a compound of formula I or a salt thereof, or of a composition thereof, for the control of pests.

In practical use for the control of arthropods, especially insects or mites, or helminths, especially nematode pests of plants, a method, for example, comprises applying to the plants or to the medium in which they grow an effective amount of a compound of the invention. For such a method, the compound of the invention is generally applied to the locus in which the arthropod or nematode infestation is to be controlled at an effective rate in the range of about 2 g to about 1 kg of the active compound per hectare of locus treated. Under ideal conditions, depending on the pest to be controlled, a lower rate may offer adequate protection. On the other hand, adverse weather conditions, resistance of the pest or other factors may require that the active ingredient be used at higher rates. The optimum rate depends usually upon a number of factors, for example, the type of pest being controlled, the type or the growth stage of the infested plant, the row spacing or also the method of application. Preferably an effective rate range of the active compound is from about 10 g/ha to about 400 g/ha, more preferably from about 50 g/ha to about 200 g/ha.

When a pest is soil-borne, the active compound generally in a formulated composition, is distributed evenly over the area to be treated (ie, for example broadcast or band treatment) in any convenient manner and is applied at rates from about 10 g ai/ha to about 400 g ai/ha, preferably from about 50 g ai/ha to about 200 g ai/ha ("ai" meaning active ingredient). When applied as a root dip to seedlings or drip irrigation to plants the liquid solution or suspension contains from about 0.075 to about 1000 mg ai/l, preferably from about 25 to about 200 mg ai/l. Application may be made, if desired, to the field or crop-growing area generally or in close proximity to the seed or plant to be protected from attack.

The compound of the invention can be washed into the soil by spraying with water over the area or can be left to the natural action of rainfall. During or after application, the formulated compound can, if desired, be distributed mechanically in the soil, for example by ploughing, disking, or use of drag chains. Application can be prior to planting, at planting, after planting but before sprouting has taken place, or after sprouting.

The compound of the invention and methods of control of pests therewith are of particular value in the protection of field, forage, plantation, glasshouse, orchard or vineyard crops, of ornamentals, or of plantation or forest trees, for example: cereals (such as wheat or rice), cotton, vegetables (such as peppers), field crops (such as sugar beets, soybeans or oil seed rape), grassland or forage crops (such as maize or sorghum), orchards or groves (such as of stone or pit fruit or citrus), ornamental plants, flowers or vegetables or shrubs under glass or in gardens or parks, or forest trees (both deciduous and evergreen) in forests, plantations or nurseries.

They are also valuable in the protection of timber (standing, felled, converted, stored or structural) from attack, for example, by sawflies or beetles or termites. They have applications in the protection of stored products such as grains, fruits, nuts, spices or tobacco, whether whole, milled or compounded into products, from moth, beetle, mite or grain weevil attack. Also protected are stored animal products such as skins, hair, wool or feathers in natural or converted form (e.g. as carpets or textiles) from moth or beetle attack as well as stored meat, fish or grains from beetle, mite or fly attack.

Additionally, the compound of the invention and methods of use thereof are of particular value in the control of arthropods or helminths which are injurious to, or spread or act as vectors of diseases domestic animals, for example those hereinbefore mentioned, and more especially in the control of ticks, mites, lice, fleas, midges, or biting, nuisance or myiasis flies. The compounds of the invention are particularly useful in controlling arthropods or helminths which are present inside domestic host animals or which feed in or on the skin or suck the blood of the animal, for which purpose they may be administered orally, parenterally, percutaneously or topically.

The compositions hereinafter described for application to growing crops or crop growing loci or as a seed dressing may, in general, alternatively be employed in the protection of stored products, household goods, property or areas of the general environment. Suitable means of applying the compounds of the invention include:

to growing crops as foliar sprays (for example as an in-furrow spray), dusts, granules, fogs or foams or also as suspensions of finely divided or encapsulated compositions as soil or root treatments by liquid drenches, dusts, granules, smokes or foams; to seeds of crops via application as seed dressings, e.g. by liquid slurries or dusts;

to animals infested by or exposed to infestation by arthropods or helminths, by parenteral, oral or topical application of compositions in which the active ingredient exhibits an immediate and/or prolonged action over a period of time against the arthropods or helminths, for example by incorporation in feed or suitable orally-ingestible pharmaceutical formulations, edible baits, salt licks, dietary supplements, pour-on formulations, sprays, baths, dips, showers, jets, dusts, greases, shampoos, creams, wax smears or livestock self-treatment systems;

to the environment in general or to specific locations where pests may lurk, including stored products, timber, household goods, or domestic or industrial premises, as sprays, fogs, dusts, smokes, wax-smears, lacquers, granules or baits, or in tricklefeeds to waterways, wells, reservoirs or other running or standing water.

The compounds of formula I or salts thereof are particularly useful for the control of parasites of animals when applied orally, and in a further preferred aspect of the invention the compounds of formula I or salts thereof are used for the control of parasites of animals by oral application.

The compounds of the formula I or salts thereof may be administered before, during or after meals. The compounds of the formula I or salts thereof may be mixed with a carrier and/or foodstuff.

The compounds of the formula I or salts thereof are administered orally in a dose to the animal in a dose range generally from 0.1 to 500 mg/kg of the compound of the formula I or salt thereof per kilogram of animal body weight (mg/kg).

The frequency of treatment of the animal, preferably the domestic animal to be treated by the compound of the formula I or salt thereof is generally from about once per week to about once per year, preferably from about once every two weeks to once every three months.

The compounds of the invention may be administered most advantageously with another parasiticidally effective material, such as an endoparasiticide, and/or an ectoparasiticide, and/or an endectoparasiticide. For example, such compounds include macrocyclic lactones such as avermectins or milbemycins e.g., ivermectin, pyratel or an insect growth regulator such as lufenuron or methoprene.

In a further preferred aspect of the invention the compounds of formula I or salts thereof are used to provide a long period of effective control of parasites of animals following a single oral application.

The compounds of the formula I or salts thereof can also be employed for controlling harmful organisms in crops of known genetically engineered plants or genetically engineered plants yet to be developed. As a rule, the transgenic plants are distinguished by especially advantageous properties, for example by resistances to particular crop protection agents, resistances to plant diseases or pathogens of plant diseases, such as particular insects or microorganisms such as fungi, bacteria or viruses. Other particular properties concern, for example, the harvested material with regard to quantity, quality, storage properties, composition and specific constituents. Thus, transgenic plants are known where the starch content is increased, or the starch quality is altered, or where the harvested material has a different fatty acid composition.

The use in economically important transgenic crops of useful plants and ornamentals is preferred, for example of cereals such as wheat, barley, rye, oats, millet, rice, cassaya and maize or else crops of sugar beet, cotton, soya, oilseed rape, potatoes, tomatoes, peas and other types of vegetables.

When used in transgenic crops, in particular those which have resistances to insects, effects are frequently observed, in addition to the effects against harmful organisms to be observed in other crops, which are specific for application in the transgenic crop in question, for example an altered or specifically widened spectrum of pests which can be controlled, or altered application rates which may be employed for application.

The invention therefore also relates to the use of compounds of the formula I or salts thereof for controlling harmful organisms in transgenic crop plants.

According to a further feature of the present invention there is provided a pesticidal composition comprising one or more compounds of the invention as defined above, in association with, and preferably homogeneously dispersed in one or more compatible pesticidally acceptable diluents or carriers and/or surface active agents (i.e. diluents or carriers and/or surface active agents of the type generally accepted in the art as being suitable for use in pesticidal compositions and which are compatible with compounds of the invention). In practice, the compounds of the invention most frequently form parts of compositions. These compositions can be employed to control arthropods, especially insects, or plant nematodes or mites. The compositions may be of any type known in the art suitable for application to the desired pest in any premises or indoor or outdoor area. These compositions contain at least one compound of the invention as the active ingredient in combination or association with one or more other compatible components which are for example, solid or liquid carriers or diluents, adjuvants, surface-active-agents, or the like appropriate for the intended use and which are agronomically or medicinally acceptable. These compositions, which may be prepared by any manner known in the art, likewise form a part of this invention. The compounds of the invention, in their commercially available formulations and in the use forms prepared from these formulations may be present in mixtures with other active substances such as insecticides, attractants, sterilants, acaricides, nematicides, fungicides, growth regulatory substances, herbicides or safeners.

Examples of co-components in mixtures are the following compounds:

Insecticides/Acaricides/Nematicides:

1. Acetylcholinesterase (AChE) inhibitors 1.1 carbamates (for example alanycarb, aldicarb, aldoxycarb, allyxycarb, aminocarb, azamethiphos, bendiocarb, benfuracarb, bufencarb, butacarb, butocarboxim, butoxycarboxim, carbaryl, carbofuran, carbosulfan, chloethocarb, coumaphos, cyanofenphos, cyanophos, dimetilan, ethiofencarb, fenobucarb, fenothiocarb, formetanate, furathiocarb, isoprocarb, metam-sodium, methiocarb, methomyl, metolcarb, oxamyl, pirimicarb, promecarb, propoxur, thiodicarb, thiofanox, triazamate, trimethacarb, XMC, xylylcarb)

1.2 organophosphates (for example acephate, azamethiphos, azinphos (-methyl, -ethyl), bromophos-ethyl, bromfenvinfos (-methyl), butathiofos, cadusafos, carbophenothion, chloroethoxyfos, chlorofenvinphos, chloromephos, chloropyrifos (-methyl/-ethyl), coumaphos, cyanofenphos, cyanophos, chlorofenvinphos, demeton-s-methyl, demeton-s-methylsulphon, dialifos, diazinon, dichlofenthion, dichlorovos/DDVP, dicrotophos, dimethoate, dimethylvinphos, dioxabenzofos, disulfoton, EPN, ethion, ethoprophos, etrimfos, famphur, fenamiphos, fenitrothion, fensulfothion, fenthion, flupyra-zofos, fonofos, formothion, fosmethilan, fosthiazate, heptenophos, iodofenphos, iprobenfos, isazofos, isofenphos, isopropyl o-salicylate, isoxathion, malathion, mecarbam, methacrifos, methamidophos, methidathion, mevinphos, monocrotophos, naled, omethoate, oxydemeton-methyl, parathion (-methyl/-ethyl), phenthoate, phorate, phosalone, phosmet, phosphamidon, phosphocarb, phoxim, pirimiphos (-methyl/-ethyl), profenofos, propaphos, propetamphos, prothiofos, prothoate, pyraclofos, pyridaphenthion, pyridathion, quinalphos, sebufos, sulfotep, sulprofos, tebupirimfos, temephos, terbufos, tetrachlorovinphos, thiometon, triazophos, triclorfon, vamidothion)

2. Sodium channel modulators/blockers of voltage-dependent sodium channels 2.1 pyrethroids (for example acrinathrin, allethrin (d-cis-trans, d-trans), beta-cyfluthrin, bifenthrin, bioallethrin, bioallethrin-S-cyclopentyl-isomer, bioethanomethrin, biopermethrin, bioresmethrin, chlovaporthrin, cis-cypermethrin, cis-resmethrin, cis-permethrin, clocythrin, cycloprothrin, cyfluthrin, cyhalothrin, cypermethrin (alpha-, beta-, theta-, zeta-), cyphenothrin, DDT, deltamethrin, empenthrin (1R-isomer), esfenvalerate, etofenprox, fenfluthrin, fenpropathrin, fenpyrithrin, fenvalerate, flubrocythrinate, flucythrinate, flufenprox, flumethrin, fluvalinate, fubfenprox, gamma-cyhalothrin, imiprothrin, kadethrin, lambda-cyhalothrin, metofluthrin, permethrin (cis-, trans-), phenothrin (1R-trans isomer), prallethrin, profluthrin, protrifenbute, pyresmethrin, resmethrin, RU 15525, silafluofen, tau-fluvalinate, tefluthrin, terallethrin, tetramethrin (1R-isomer), tralomethrin, transfluthrin, ZXI 8901, pyrethrins (pyrethrum))

2.2 oxadiazines (for example indoxacarb)

3. Acetylcholine receptor agonists/antagonists
3.1 chloronicotinyls/neonicotinoids (for example acetamiprid, clothianidin, dinotefuran, imidacloprid, nitenpyram, nithiazine, thiacloprid, thiamethoxam)
3.2 nicotine, bensultap, cartap
4. Acetylcholine receptor modulators
4.1 spinosyns (for example spinosad)
5. Antagonists of GABA-controlled chloride channels
5.1 cyclodiene organochlorines (for example camphechloro, chlorodane, endosulfan, gamma-HCH, HCH, heptachloro, lindane, methoxychloro
5.2 fiproles (for example acetoprole, ethiprole, fipronil, vaniliprole)
6. chloride channel activators
6.1 mectins (for example abamectin, avermectin, emamectin, emamectin-benzoate, ivermectin, milbemectin, milbemycin)
7. Juvenile hormone mimetics (for example diofenolan, epofenonane, fenoxycarb, hydroprene, kinoprene, methoprene, pyriproxifen, triprene)
8. Ecdyson agonists/disruptors
8.1 diacylhydrazines (for example chromafenozide, halofenozide, methoxyfenozide, tebufenozide)
9. Chitin biosynthesis inhibitors
9.1 benzoylureas (for example bistrifluoron, chlofluazuron, diflubenzuron, fluazuron, flucycloxuron, flufenoxuron, hexaflumuron, lufenuron, novaluron, noviflumuron, penfluoron, teflubenzuron, triflumuron)
9.2 buprofezin
9.3 cyromazine
10. Inhibitors of oxidative phosphorylation, ATP disruptors
10.1 diafenthiuron
10.2 organotins (for example azocyclotin, cyhexatin, fenbutatin-oxide)
11. Decouplers of oxidative phosphorylation acting by interrupting the H-proton gradient
11.1 pyrroles (for example chlorfenapyr)
11.2 dinitrophenols (for example binapacryl, dinobuton, dinocap, DNOC)
12. Site-I electron transport inhibitors
12.1 METIs (for example fenazaquin, fenpyroximate, pyrimidifen, pyridaben, tebufenpyrad, tolfenpyrad)
12.2 hydramethylnone
12.3 dicofol
13. Site-II electron transport inhibitors
13.1 rotenone
14. Site-III electron transport inhibitors
14.1 acequinocyl, fluacrypyrim
15. Microbial disruptors of the insect gut membrane
*Bacillus thuringiensis* strains
16. Inhibitors of fat synthesis
16.1 tetronic acids (for example spirodiclofen, spiromesifen)
16.2 tetramic acids [for example 3-(2,5-dimethylphenyl)-8-methoxy-2-oxo-1-azaspiro[4.5]dec-3-en-4-yl ethyl carbonate (alias: carbonic acid, 3-(2,5-dimethylphenyl)-8-methoxy-2-oxo-1-azaspiro[4.5]dec-3-en-4-yl ethyl ester, CAS Reg. No.: 382608-10-8) and carbonic acid, cis-3-(2, 5-dimethylphenyl)-8-methoxy-2-oxo-1-azaspiro[4.5]dec-3-en-4-yl ethyl ester (CAS Reg. No.: 203313-25-1)]
17. Carboxamides
(for example flonicamid)
18. Octopaminergic agonists
(for example amitraz)
19. Inhibitors of magnesium-stimulated ATPase
(for example propargite)
20. Phthalamides
(for example $N^2$-[1,1-dimethyl-2-(methylsulphonyl)ethyl]-3-iodo-$N^1$-[2-methyl-4-[1,2,2,2-tetrafluoro-1-(trifluoromethyl)ethyl]phenyl]-1,2-benzenedicarboxamide (CAS Reg. No.: 272451-65-7), flubendiamide)
21. Nereistoxin analogues
(for example thiocyclam hydrogen oxalate, thiosultap-sodium)
22. Biologicals, hormones or pheromones
(for example azadirachtin, *Bacillus* spec., *Beauveria* spec., *Codlemone, Metarrhizium* spec., *Paecilomyces* spec., *Thuringiensin, Verticillium* spec.)
23. Active compounds with unknown or unspecific mechanisms of action
23.1 fumigants (for example aluminium phosphide, methyl bromide, sulphuryl fluoroide)
23.2 selective antifeedants (for example cryolite, flonicamid, pymetrozine)
23.3 mite growth inhibitors (for example clofentezine, etoxazole, hexythiazox)
23.4 amidoflumet, benclothiaz, benzoximate, bifenazate, bromopropylate, buprofezin, chinomethionat, chlorodimeform, chlorobenzilate, chloropicrin, clothiazoben, cycloprene, cyflumetofen, dicyclanil, fenoxacrim, fentrifanil, flubenzimine, flufenerim, flutenzin, gossyplure, hydramethylnone, japonilure, metoxadiazone, petroleum, pipero- nyl butoxide, potassium oleate, pyrafluprole, pyridalyl, pyriprole, sulfluramid, tetradifon, tetrasul, triarathene, verbutin, furthermore the compound 3-methylphenyl propylcarbamate (Tsumacide Z), the compound 3-(5-chloro-3-pyridinyl)-8-(2,2,2-trifluoroethyl)-8-azabicyclo[3.2.1]-octane-3-carbonitrile (CAS Reg. No. 185982-80-3) and the corresponding 3-endo-isomer (CAS Reg. No. 185984-60-5) (cf. WO 96/37494, WO 98/25923), and preparations which comprise insecticidally active plant extracts, nematodes, fungi or viruses.

Fungicides:
1. Inhibition of Nucleic acid synthesis
1.1 benalaxyl, benalaxyl-M, bupirimate, chiralaxyl, clozylacon, dimethirimol, ethirimol, furalaxyl, hymexazol, metalaxyl-M, ofurace, oxadixyl, oxolinic acid
2. Inhibition of mitosis and cell division:
2.1 benomyl, carbendazim, diethofencarb, fuberidazole, pencycuron, thiabendazole thiophanate-methyl, zoxamide
3. Inhibition of respiration
3.1 CI: diflumetorim
3.2 CII: boscalid, carboxin, fenfuram, flutolanil, furametpyr, mepronil, oxycarboxine, penthiopyrad, thifluzamide
3.3 CII: azoxystrobin, cyazofamid, dimoxystrobin, enestrobin, famoxadone, fenamidone, fluoxastrobin, kresoxim-methyl, metominostrobin, orysastrobin, pyraclostrobin, picoxystrobin, trifloxystrobin,
3.4 Uncouplers: dinocap, fluazinam
3.5 Inhibition of ATP production: fentin acetate, fentin chloride, fentin hydroxide, silthiofam
4. Inhibition of AA and protein biosynthesis
4.1 andoprim, blasticidin-S, cyprodinil, kasugamycin, kasugamycin hydrochloride hydrate, mepanipyrim, pyrimethanil,
5. Inhibition of signal transduction
5.1 fenpiclonil, fludioxonil, quinoxyfen 6. Inhibition of lipids and membranes synthesis
6.1 chlozolinate, iprodione, procymidone, vinclozolin
6.2 pyrazophos, edifenphos, iprobenfos (IBP), isoprothiolane
6.3 tolclofos-methyl, biphenyl
6.4 iodocarb, propamocarb, propamocarb hydrochloride
7. Inhibition of ergosterol Biosynthesis
7.1 fenhexamid
7.2 azaconazole, bitertanol, bromuconazole, cyproconazole, diclobutrazole, difenoconazole, diniconazole, diniconazole-M, epoxiconazole, etaconazole, fenbuconazole, fluquinconazole, flusilazole, flutriafol, furconazole, furconazole-cis, hexaconazole, imibenconazole, ipconazole, metconazole, myclobutanil, paclobutrazol, penconazole, propiconazole, prothioconazole, simeconazole, tebuconazole, tetraconazole, triadimefon, triadimenol, triticonazole, uniconazole, voriconazole, imazalil, imazalil sulfate, oxpoconazole, fenarimol, flurprimidol, nuarimol, pyrifenox, triforine, pefurazoate, prochloraz, triflumizole, viniconazole,
7.3 aidimorph, dodemorph, dodemorph acetate, fenpropimorph, tridemorph, fenpropidin, spiroxamine
7.4 naftifine, pyributicarb, terbinafine,
8. Inhibition of cell wall synthesis
8.1 benthiavalicarb, bialaphos, dimethomorph, flumorph, iprovalicarb, polyoxins, polyoxorim, validamycin A
9. Inhibition of melanine biosynthesis
9.1 carpropamid, diclocymet, fenoxanil, phtalide, pyroquilon, tricyclazole,
10. Host defence inducer
10.1 acibenzolar-S-methyl, probenazole, tiadinil
11. Multisite
11.1 captafol, captan, chlorothalonil, copper preparations such as: copper hydroxide, copper naphthenate, copper oxychloride, copper sulphate, copper oxide, oxine-copper and Bordeaux mixture, dichlofluanid, dithianon, dodine, dodine free base, ferbam, fluorofolpet, folpet, guazatine, guazatien acetate, iminoctadine, iminoctadine albesilate, iminoctadine triacetate, mancopper, mancozeb, maneb, metiram, metiram zinc, propineb, sulphur and sulphur preparations including calcium polysulphide, thiram, tolylfluanid, zineb, ziram,
12. Unknown
12.1 amibromdole, benthiazole, bethoxazin, capsimycin, carvone, chinomethionat, chloropicrin, cufraneb, cyflufenamid, cymoxanil, dazomet, debacarb, diclomezine, dichlorophen, dicloran, difenzoquat, difenzoquat methylsulphate, diphenylamine, ethaboxam, ferimzone, flumetover, flusulfamide, fosetyl-aluminium, fosetyl-calcium, fosetyl-sodium, fluopicolide, fluoroimide, hexachlorobenzene, 8-hydroxyquinoline sulfate, irumamycin, methasulphocarb, metrafenone, methyl isothiocyanate, mildiomycin, natamycin, nickel dimethyldithiocarbamate, nitrothal-isopropyl, octhilinone, oxamocarb, oxyfenthiin, pentachlorophenol and salts, 2-phenylphenol and salts, phosphorous acid and its salts, piperalin, propanosine-sodium, proquinazid, pyrrolnitrine, quintozene, tecloftalam, tecnazene, triazoxide, trichlamide, zarilamid and 2,3,5,6-tetrachloro-4-(methylsulfonyl)-pyridine, N-(4-Chloro-2-nitrophenyl)-N-ethyl-4-methyl-benzenesulfonamide, 2-amino-4-methyl-N-phenyl-5-thiazolecarboxamide, 2-chloro-N-(2,3-dihydro-1,1,3-trimethyl-1H-inden-4-yl)-3-pyridincarboxamide, 3-[5-(4-chlorophenyl)-2,3-dimethylisoxazolidin-3-yl]pyridine, cis-1-(4-chlorophenyl)-2-(1H-1,2,4-triazole-1-yl)-cycloheptanol, methyl 1-(2,3-dihydro-2,2-dimethyl-1H-inden-1-yl)-1H-imidazole-5-carboxylate, 3,4,5-trichloro-2,6-pyridinedicarbonitrile, Methyl 2-[[[cyclopropyl[(4-methoxyphenyl)imino]methyl]thio]methyl]-.alpha.-(methoxy-methylene)-benzeneacetate, 4-Chloro-alpha-propynyloxy-N-[2-[3-methoxy-4-(2-propynyloxy)phenyl]ethyl]-benzeneacetamide, (2S)—N-[2-[4-[[3-(4-chlorophenyl)-2-propynyl]oxy]-3-methoxyphenyl]ethyl]-3-methyl-2-[(methylsulfonyl)amino]-butanamide, 5-chloro-7-(4-methylpiperidin-1-yl)-6-(2,4,6-trifluorophenyl)[1,2,4]triazolo[1,5-a]pyrimidine, 5-chloro-6-(2,4,6-trifluorophenyl)-N-[(1R)-1,2,2-trimethylpropyl][1,2,4]triazolo[1,5-a]pyrimidin-7-amine, 5-chloro-N-[(1R)-1,2-dimethylpropyl]-6-(2,4,6-trifluorophenyl)[1,2,4]triazolo[1,5-a]pyrimidin-7-amine, N-[1-(5-bromo-3-chloropyridin-2-yl)ethyl]-2,4-dichloronicotinamide, N-(5-bromo-3-chloropyridin-2-yl)methyl-2,4-dichloronicotinamide, 2-butoxy-6-iodo-3-propyl-benzopyranon-4-one, N-{(Z)-[(cyclopropylmethoxy)imino][6-(difluoromethoxy)-2,3-difluorophenyl]methyl}-2-phenyl-acetamide, N-(3-ethyl-3,5,5-trimethyl-cyclohexyl)-3-formylamino-2-hydroxy-benzamide, 2-[[[[1-[3(1 Fluoro-2-phenylethyl)oxy]phenyl]ethylidene]amino]oxy]methyl]-alpha-(methoxyimino)-N-methyl-alphaE-benzeneacetamide, N-{2-[3-chloro-5-(trifluoromethyl)pyridin-2-yl]ethyl}-2-(trifluoromethyl) benzamide, N-(3',4'-dichloro-5-fluorobiphenyl-2-yl)-3-(difluoromethyl)-1-methyl-1H-pyrazole-4-carboxamide, 1-[(4-methoxyphenoxy)methyl]-2,2-dimethylpropyl-1H-imidazole-1-carboxylic acid, O-[1-[(4-methoxyphenoxy)methyl]-2,2-dimethylpropyl]-1H-imidazole-1-carbothioic acid, 2-(2-{[6-(3-chloro-2-methylphenoxy)-5-fluoropyrimidin-4-yl]oxy}phenyl)-2-(methoxyimino)-N-methylacetamide Bactericides:
bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

The abovementioned components for combinations are known active substances, many of which are described in Ch. R Worthing, S. B. Walker, The Pesticide Manual, 13$^{th}$ Edition, British Crop Protection Council, Farnham 2003.

The effective use doses of the compounds employed in the invention can vary within wide limits, particularly depending on the nature of the pest to be eliminated or degree of infestation, for example, of crops with these pests. In general, the compositions according to the invention usually contain about 0.05 to about 95% (by weight) of one or more active ingredients according to the invention, about 1 to about 95% of one or more solid or liquid carriers and, optionally, about 0.1 to about 50% of one or more other compatible components, such as surface-active agents or the like.

In the present account, the term "carrier" denotes an organic or inorganic ingredient, natural or synthetic, with which the active ingredient is combined to facilitate its application, for example, to the plant, to seeds or to the soil. This carrier is therefore generally inert and it must be acceptable (for example, agronomically acceptable, particularly to the treated plant).

The carrier may be a solid, for example, clays, natural or synthetic silicates, silica, resins, waxes, solid fertilizers (for example ammonium salts), ground natural minerals, such as kaolins, clays, talc, chalk, quartz, attapulgite, montmorillonite, bentonite or diatomaceous earth, or ground synthetic minerals, such as silica, alumina, or silicates especially aluminium or magnesium silicates. As solid carriers for granules the following are suitable: crushed or fractionated natural rocks such as calcite, marble, pumice, sepiolite and dolomite; synthetic granules of inorganic or organic meals; granules of organic material such as sawdust, coconut shells, corn cobs, corn husks or tobacco stalks; kieselguhr, tricalcium phosphate, powdered cork, or absorbent carbon black; water soluble polymers, resins, waxes; or solid fertilizers. Such solid compositions may, if desired, contain one or more compatible wetting, dispersing, emulsifying or colouring agents which, when solid, may also serve as a diluent.

The carrier may also be liquid, for example: water; alcohols, particularly butanol or glycol, as well as their ethers or esters, particularly methylglycol acetate; ketones, particularly acetone, cyclohexanone, methylethyl ketone, methyl-iso-butylketone, or isophorone; petroleum fractions such as paraffinic or aromatic hydrocarbons, particularly xylenes or alkyl naphthalenes; mineral or vegetable oils; aliphatic chlorinated hydrocarbons, particularly trichloroethane or methylene chloride; aromatic chlorinated hydrocarbons, particularly chlorobenzenes; water-soluble or strongly polar solvents such as dimethylformamide, dimethyl sulphoxide, or N-methylpyrrolidone; liquefied gases; or the like or a mixture thereof.

The surface-active agent may be an emulsifying agent, dispersing agent or wetting agent of the ionic or non-ionic type or a mixture of such surface-active agents. Amongst these are e.g., salts of polyacrylic acids, salts of lignosulphonic acids, salts of phenolsulphonic or naphthalenesulphonic acids, polycondensates of ethylene oxide with fatty alcohols or fatty acids or fatty esters or fatty amines, substituted phenols (particularly alkylphenols or arylphenols), salts of sulphosuccinic acid esters, taurine derivatives (particularly alkyltaurates), phosphoric esters of alcohols or of polycondensates of ethylene oxide with phenols, esters of fatty acids with polyols, or sulphate, sulphonate or phosphate functional derivatives of the above compounds. The presence of at least one surface-active agent is generally essential when the active ingredient and/or the inert carrier are only slightly water soluble or are not water soluble and the carrier agent of the composition for application is water.

Compositions of the invention may further contain other additives such as adhesives or colorants. Adhesives such as carboxymethylcellulose or natural or synthetic polymers in the form of powders, granules or lattices, such as arabic gum, polyvinyl alcohol or polyvinyl acetate, natural phospholipids, such as cephalins or lecithins, or synthetic phospholipids can be used in the formulations. It is possible to use colorants such as inorganic pigments, for example: iron oxides, titanium oxides or Prussian Blue; organic dyestuffs, such as alizarin dyestuffs, azo dyestuffs or metal phthalocyanine dyestuffs; or trace nutrients such as salts of iron, manganese, boron, copper, cobalt, molybdenum or zinc.

For their agricultural application, the compounds of the invention are therefore generally in the form of compositions, which are in various solid or liquid forms.

Solid forms of compositions which can be used are dusting powders (with a content of the compound of the invention, ranging up to 80%), wettable powders or granules (including water dispersible granules), particularly those obtained by extrusion, compacting, impregnation of a granular carrier, or granulation starting from a powder (the content of the compound of the invention, in these wettable powders or granules being between about 0.5 and about 80%). Solid homogenous or heterogenous compositions containing one or more compounds of the invention, for example granules, pellets, briquettes or capsules, may be used to treat standing or running water over a period of time. A similar effect may be achieved using trickle or intermittent feeds of water dispersible concentrates as described herein.

Liquid compositions, for example, include aqueous or non-aqueous solutions or suspensions (such as emulsifiable concentrates, emulsions, flowables, dispersions, or solutions) or aerosols. Liquid compositions also include, in particular, emulsifiable concentrates, dispersions, emulsions, flowables, aerosols, wettable powders (or powder for spraying), dry flowables or pastes as forms of compositions which are liquid or intended to form liquid compositions when applied, for example as aqueous sprays (including low and ultra-low volume) or as fogs or aerosols.

Liquid compositions, for example, in the form of emulsifiable or soluble concentrates most frequently comprise about 5 to about 80% by weight of the active ingredient, while the emulsions or solutions which are ready for application contain, in their case, about 0.01 to about 20% of the active ingredient. Besides the solvent, the emulsifiable or soluble concentrates may contain, when required, about 2 to about 50% of suitable additives, such as stabilizers, surface-active agents, penetrating agents, corrosion inhibitors, colorants or adhesives. Emulsions of any required concentration, which are particularly suitable for application, for example, to plants, may be obtained from these concentrates by dilution with water. These compositions are included within the scope of the compositions which may be employed in the present invention. The emulsions may be in the form of water-in-oil or oil-in-water type and they may have a thick consistency.

The liquid compositions of this invention may, in addition to normal agricultural use applications be used for example to treat substrates or sites infested or liable to infestation by arthropods (or other pests controlled by compounds of this invention) including premises, outdoor or indoor storage or processing areas, containers or equipment or standing or running water.

All these aqueous dispersions or emulsions or spraying mixtures can be applied, for example, to crops by any suitable means, chiefly by spraying, at rates which are generally of the order of about 100 to about 1,200 liters of spraying mixture per hectare, but may be higher or lower (eg. low or ultra-low volume) depending upon the need or application technique. The compound or compositions according to the invention are conveniently applied to vegetation and in particular to roots or leaves having pests to be eliminated. Another method of application of the compounds or compositions according to the invention is by chemigation, that is to say, the addition of a formulation containing the active ingredient to irrigation water. This irrigation may be sprinkler irrigation for foliar pesticides or it can be ground irrigation or underground irrigation for soil or for systemic pesticides.

The concentrated suspensions, which can be applied by spraying, are prepared so as to produce a stable fluid product which does not settle (fine grinding) and usually contain from about 10 to about 75% by weight of active ingredient, from about 0.5 to about 30% of surface-active agents, from about 0.1 to about 10% of thixotropic agents, from about 0 to about 30% of suitable additives, such as anti-foaming agents, corrosion inhibitors, stabilizers, penetrating agents, adhesives and, as the carrier, water or an organic liquid in which the active ingredient is poorly soluble or insoluble Some organic solids or inorganic salts may be dissolved in the carrier to help prevent settling or as antifreezes for water.

The wettable powers (or powder for spraying) are usually prepared so that they contain from about 10 to about 80% by weight of active ingredient, from about 20 to about 90% of a solid carrier, from about 0 to about 5% of a wetting agent, from about 3 to about 10% of a dispersing agent and, when necessary, from about 0 to about 80% of one or more stabilizers and/or other additives, such as penetrating agents, adhesives, anti-caking agents, colorants, or the like. To obtain these wettable powders, the active ingredient is thoroughly mixed in a suitable blender with additional substances which may be impregnated on the porous filler and is ground using a mill or other suitable grinder. This produces wettable powders, the wettability and the suspendability of which are advantageous. They may be suspended in water to give any desired concentration and this suspension can be employed very advantageously in particular for application to plant foliage.

The "water dispersible granules (WG)" (granules which are readily dispersible in water) have compositions which are substantially close to that of the wettable powders. They may be prepared by granulation of formulations described for the wettable powders, either by a wet route (contacting finely divided active ingredient with the inert filler and a little water, e.g. 1 to 20% by weight, or with an aqueous solution of a dispersing agent or binder, followed by drying and screening), or by a dry route (compacting followed by grinding and screening). The rates and concentrations of the formulated compositions may vary according to the method of application or the nature of the compositions or use thereof. Generally speaking, the compositions for application to control arthropod or plant nematode pests usually contain from about 0.00001% to about 95%, more particularly from about 0.0005% to about 50% by weight of one or more compounds of the invention, or of total active ingredients (that is to say the compounds of the invention, together with other substances toxic to arthropods or plant nematodes, synergists, trace elements or stabilizers). The actual compositions employed and their rate of application will be selected to achieve the desired effect(s) by the farmer, livestock producer, medical or veterinary practitioner, pest control operator or other person skilled in the art. Solid or liquid compositions for application topically to animals, timber, stored products or household goods usually contain from about 0.00005% to about 90%, more particularly from about 0.001% to about 10%, by weight of one or more compounds of the invention. For administration to animals orally or parenterally, including percutaneously solid or liquid compositions, these normally contain from about 0.1% to about 90% by weight of one or more compounds of the invention. Medicated feedstuffs normally contain from about 0.001% to about 3% by weight of one or more compounds of the invention. Concentrates or supplements for mixing with feedstuffs normally contain from about 5% to about 90%, preferably from about 5% to about 50%, by weight of one or more compounds of the invention. Mineral salt licks normally contain from about 0.1% to about 10% by weight of one or more compounds of formula (I) or pesticidally acceptable salts thereof.

Dusts or liquid compositions for application to livestock, goods, premises or outdoor areas may contain from about 0.0001% to about 15%, more especially from about 0.005% to about 2.0%, by weight, of one or more compounds of the invention. Suitable concentrations in treated waters are between about 0.0001 ppm and about 20 ppm, more particularly about 0.001 ppm to about 5.0 ppm. of one or more compounds of the invention, and may be used therapeutically in fish farming with appropriate exposure times. Edible baits may contain from about 0.01% to about 5%, preferably from about 0.01% to about 1.0%, by weight of one or more compounds of the invention.

When administered to vertebrates parenterally, orally or by percutaneous or other means, the dosage of compounds of the invention, will depend upon the species, age, or health of the vertebrate and upon the nature and degree of its actual or potential infestation by arthropod or helminth pests. A single dose of about 0.1 to about 100 mg, preferably about 2.0 to about 20.0 mg, per kg body weight of the animal or doses of about 0.01 to about 20.0 mg, preferably about 0.1 to about 5.0 mg, per kg body weight of the animal per day, for sustained medication, are generally suitable by oral or parenteral administration. By use of sustained release formulations or devices, the daily doses required over a period of months may be combined and administered to animals on a single occasion.

The following composition EXAMPLES 2A-2M illustrate compositions for use against arthropods, especially mites or insects, or plant nematodes, which comprise, as active ingredient, compounds of the invention, such as those described in preparative examples. The compositions described in EXAMPLES 2A-2M can each be diluted to give a sprayable compositon at concentrations suitable for use in the field. Generic chemical descriptions of the ingredients (for which all of the following percentages are in weight percent), used in the composition EXAMPLES 2A-2M exemplified below, are as follows:

| Trade Name | Chemical Description |
|---|---|
| Ethylan BCP | Nonylphenol ethylene oxide condensate |
| Soprophor BSU | Tristyrylphenol ethylene oxide condensate |
| Arylan CA | A 70% w/v solution of calcium dodecylbenzenesulfonate |
| Solvesso 150 | Light $C_{10}$ aromatic solvent |
| Arylan S | Sodium dodecylbenzenesulfonate |
| Darvan $NO_2$ | Sodium lignosulphonate |
| Celite PF | Synthetic magnesium silicate carrier |
| Sopropon T36 | Sodium salts of polycarboxylic acids |
| Rhodigel 23 | Polysaccharide xanthan gum |
| Bentone 38 | Organic derivative of magnesium montmorillonite |
| Aerosil | Microfine silicon dioxide |

Example 2A

| | |
|---|---|
| Active ingredient | 7% |
| Ethylan BCP | 10% |
| N-methylpyrrolidone | 83% |

A water soluble concentrate is prepared with the composition as follows: To a solution of Ethylan BCP dissolved in a portion of N-methylpyrrolidone is added the active ingredient with heating and stirring until dissolved. The resulting solution is made up to volume with the remainder of the solvent.

Example 2B

An emulsifiable concentrate (EC) is prepared with the composition as follows:

| | |
|---|---|
| Active ingredient | 25%(max) |
| Soprophor BSU | 10% |
| Arylan CA | 5% |
| N-methylpyrrolidone | 50% |
| Solvesso 150 | 10% |

The first three components are dissolved in N-methylpyrrolidone and to this is then added the Solvesso 150 to give the final volume.

Example 2C

A wettable powder (WP) is prepared with the composition as follows:

| | |
|---|---|
| Active ingredient | 40% |
| Arylan S | 2% |
| Darvan NO$_2$ | 5% |
| Celite PF | 53% |

The ingredients are mixed and ground in a hammer-mill to a powder with a particle size of less than 50 microns.

Example 2D

An aqueous-flowable formulation is prepared with the composition as follows:

| | |
|---|---|
| Active ingredient | 40.00% |
| Ethylan BCP | 1.00% |
| Sopropon T360 | 0.20% |
| Ethylene glycol | 5.00% |
| Rhodigel 230. | 0.15% |
| Water | 53.65% |

The ingredients are intimately mixed and are ground in a bead mill until a mean particle size of less than 3 microns is obtained.

Example 2E

An emulsifiable suspension concentrate is prepared with the composition as follows:

| | |
|---|---|
| Active ingredient | 30.0% |
| Ethylan BCP | 10.0% |
| Bentone 38 | 0.5% |
| Solvesso 150 | 59.5% |

The ingredients are intimately mixed and ground in a bead-mill until a mean particle size of less than 3 microns is obtained.

Example 2F

A water dispersible granule is prepared with the composition as follows:

| | |
|---|---|
| Active ingredient | 30% |
| Darvan No 2 | 15% |
| Arylan S | 8% |
| Celite PF | 47% |

The ingredients are mixed, micronized in a fluid-energy mill and then granulated in a rotating pelletizer by spraying with water (up to 10%). The resulting granules are dried in a fluid-bed drier to remove excess water.

Example 2G

A dusting powder is prepared with the composition as follows:

| | |
|---|---|
| Active ingredient | 1 to 10% |
| Talc powder-superfine | 99 to 90% |

The ingredients are intimately mixed and further ground as necessary to achieve a fine powder. This powder may be applied to a locus of arthropod infestation, for example refuse dumps, stored products or household goods or animals infested by, or at risk of infestation by, arthropods to control the arthropods by oral ingestion. Suitable means for distributing the dusting powder to the locus of arthropod infestation include mechanical blowers, handshakers or livestock self treatment devices.

Example 2H

An edible bait is prepared with the composition as follows:

| | |
|---|---|
| Active ingredient | 0.1 to 1.0% |
| Wheat flour | 80% |
| Molasses | 19.9 to 19% |

The ingredients are intimately mixed and formed as required into a bait form. This edible bait may be distributed at a locus, for example domestic or industrial premises, e.g. kitchens, hospitals or stores, or outdoor areas, infested by arthropods, for example ants, locusts, cockroaches or flies, to control the arthropods by oral ingestion.

Example 2I

A solution formulation is prepared with a composition as follows:

| | |
|---|---|
| Active ingredient | 15% |
| Dimethyl sulfoxide | 85% |

The active ingredient is dissolved in dimethyl sulfoxide with mixing and or heating as required. This solution may be applied percutaneously as a pour-on application to domestic animals infested by arthropods or, after sterilization by filtration through a polytetrafluoroethylene membrane (0.22 micrometer pore size), by parenteral injection, at a rate of application of from 1.2 to 12 ml of solution per 100 kg of animal body weight.

Example 2J

A wettable powder is prepared with the composition as follows:

| | |
|---|---|
| Active ingredient | 50% |
| Ethylan BCP | 5% |
| Aerosil | 5% |
| Celite PF | 40% |

The Ethylan BCP is absorbed onto the Aerosil which is then mixed with the other ingredients and ground in a hammer-mill to give a wettable powder, which may be diluted with water to a concentration of from 0.001% to 2% by weight of the active compound and applied to a locus of infestation by arthropods, for example, dipterous larvae or plant nematodes, by spraying, or to domestic animals infested by, or at risk of infection by arthropods, by spraying or dipping, or by oral administration in drinking water, to control the arthropods.

Example 2K

A slow release bolus composition is formed from granules containing the following components in varying percentages (similar to those described for the previous compositions) depending upon need:

| |
|---|
| Active ingredient |
| Density agent |
| Slow-release agent |
| Binder |

The intimately mixed ingredients are formed into granules which are compressed into a bolus with a specific gravity of 2 or more. This can be administered orally to ruminant domestic animals for retention within the reticulo-rumen to give a continual slow release of active compound over an extended period of time to control infestation of the ruminant domestic animals by arthropods.

Example 2L

A slow release composition in the form of granules, pellets, brickettes or the like can be prepared with compositions as follows:

| | |
|---|---|
| Active ingredient | 0.5 to 25% |
| Polyvinyl chloride | 75 to 99.5% |
| Dioctyl phthalate (plasticizer) | |

The components are blended and then formed into suitable shapes by melt-extrusion or molding. These composition are useful, for example, for addition to standing water or for fabrication into collars or eartags for attachment to domestic animals to control pests by slow release.

Example 2M

A water dispersible granule is prepared with the composition as follows:

| | |
|---|---|
| Active ingredient | 85%(max) |
| Polyvinylpyrrolidone | 5% |
| Attapulgite clay | 6% |
| Sodium lauryl sulfate | 2% |
| Glycerine | 2% |

The ingredients are mixed as a 45% slurry with water and wet milled to a particle size of 4 microns, then spray-dried to remove water.

Methods of Pesticidal Use

The following representative test procedure, using compounds of the invention, was conducted to determine the insecticidal and parasiticidal activities of compound of the invention.

METHOD A: Screening method to test systemicity of compounds against *Ctenocephalides felis* (Cat flea)

A test container was filled with 10 adults of *Ctenocephalides felis*. A glass cylinder was closed on one end with parafilm and placed on top of the test container. The test compound solution was then pipetted into bovine blood and added to the glass cylinder. The treated *Ctenocephalides felis* were held in this artificial dog test (blood 37° C., 40-60% relative humidity; *Ctenocephalides felis* 20-22° C., 40-60% relative humidity) and assessment performed at 24 and 48 hours after application.

Compound numbers 1-1 gave at least 50% control of *Ctenocephalides felis* at a test concentration of 1 ppm.

Intermediate Example 2 of formula III gave at least 70% control of *Ctenocephalides felis* at a test concentration of 1 ppm.

METHOD B: *Diabrotica undecimpunctata* (southern corn rootworm) screen

Two days before application, seeds of maize were soaked in water under warm conditions to elicit fast germination. One day before application, eggs of *Diabrotica undecimpunctata* were transferred to one half of a Japanese filter paper placed in a plastic petri dish. Afterwards, a sprouted maize seed was placed on a moistened pad beside the filter paper. Three drops of 200 microlitres of test compound solution were carefully pipetted onto the egg. The remainder of the solution was placed on the maize and then the Petri dish was closed. The treated eggs in the Petri dishes were held in a climate chamber for 6 days. The compound efficacy (percentage of dead eggs and/or larvae in comparison to untreated control) was assessed 6 days after application using a binocular microscope. Compound number 1-1 gave at least 60% control with the concentration at 10 ppm.

METHOD C: Rice leafhopper screen

The leaves of rice plants are dipped for 5 seconds into an aqueous solution of the formulated preparation to be examined. After the solution has run off, the rice plants are placed in a Petri dish and populated with about 20 larvae (L3 stage) of the rice leafhopper species *Nilaparvata lugens*. The Petri dish is closed and then stored in a climatized chamber (16 hours of light/day, 25° C., 40-60% relative atmospheric humidity). After 6 days storage, the mortality among the leafhopper larvae is determined. Compound number 1-1 gave at least 60% control of *Nilaparvata lugens* with the concentration of 10 ppm.

METHOD D: Screening method to test contact activity against *Rhipicephalus sanguineus* (Brown dog tick)

Solutions of the test compounds were dropped onto filter paper, dried and the filter paper placed into test tubes and infested with 20-30 larvae (L1) of *Rhipicephalus sanguineus* and the tubes closed with a clip. The treated *Rhipicephalus sanguineus* were held in a climate chamber (25° C., 90% RH) and the percentage efficacy assessed 24 hours after application in comparison with the untreated control.

Compound 1-1 provided at least 50% of control with the test concentration at 10 ppm.

METHOD E: *Heliothis Virescens* Screen

A Petri dish whose bottom is covered with filter paper and which contains about 5 ml of culture medium is prepared. Pieces of filter paper with about 30, 24-hour-old eggs of the tobacco budworm (*Heliothis virescens*) are dipped into an aqueous solution of the formulated preparation to be examined for about 5 seconds and subsequently placed into the Petri dish. A further 200 µl of the aqueous solution are dropped over the culture medium. The Petri dish is closed and then kept at about 25° C. in a climatized chamber. After 6 days storage, the effect of the preparation on the eggs and the larvae which may have hatched from these is determined. Compound number 1-1 gave at least 50% control of tobacco budworm with the concentration at 100 ppm.

METHOD F: Thrip (*Frankliniella occidentalis*) Screen

French bean plants are cut at the base of the stem and transferred into bottles filled with tap water. The leaves are then dipped for 5 seconds into an aqueous solution of the formulated preparation to be examined. After the solution has run off, the leaves are infested with 20-30 individuals of a mixed population of flower thrips (*Frankliniella occidentalis*) and then stored in a controlled-environment cabinet at approx. 25° C. After 7 days storage, the effect of the preparation on the thrips is determined. Compound number 1-1 gave at least 70% control of *Frankliniella occidentalis* at the concentration of 100 ppm.

The invention claimed is:

1. A compound which is a 5-(vinylamino)pyryazole derivative of formula I or a pesticidally acceptable salt thereof

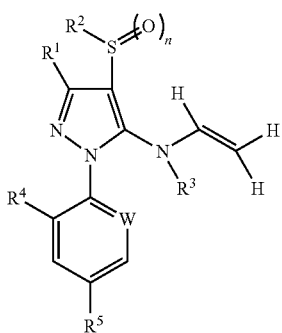

(I)

wherein

W is CH, $CR^6$ or $C(NR^7R^8)$;

$R^6$ is halogen or haloalkyl, $R^7$ and $R^8$ are independently of one another hydrogen, alkyl, cycloalkyl, aryl, heterocyclyl, aralkyl or heterocyclylalkyl, or one of $R^7$ or $R^5$ are CO—$R^{7a}$, —COO—O—$R^{8a}$—SO—$R^{7a}$ or $SO_2R^{7a}$, or $R^7$ and $R^8$ together with the attached N-atom form a five- to seven-membered heterocyclic ring which optionally contains an additional oxygen, sulfur or nitrogen atom in the ring or $R^7$ and $R^8$ together with the attached N-atom form an imine group N=$CR^{7b}R^{8b}$ or an iminoether group —N=$CR^{7b}(OR^{8b})$, $R^{7a}$ and $R^{8a}$ are alkyl, cycloalkyl, aryl, heterocyclyl, aralkyl or heterocyclylalkyl, $R^{7b}$ is hydrogen, alkyl, cycloalkyl, aryl, heterocyclyl, aralkyl or heterocyclylalkyl, $R^{8b}$ is alkyl, cycloalkyl, aryl, heterocyclyl, aralkyl or heterocyclylalkyl, which groups $R^7$, $R^8$, $R^{7a}$, $R^{8a}$, $R^{7b}$ and $R^{8b}$ independently of one another are optionally substituted by one or more halogen atoms, hydroxyl, oxo, cyano, nitro, alkyl, alkoxy, alkylthio, cycloalkyl, aryl, heterocyclyl, aralkyl or heterocyclylalkyl groups or by amino, which is optionally substituted by alkyl, alkenyl, alkynyl, aryl or heteroaryl groups;

$R^1$ is cyano, halogen, or —CS—$NH_2$, $R^2$ is alkyl or cycloalkyl, which group $R^2$ is optionally substituted by one or more halogen atoms, hydroxyl, oxo, alkyl, alkoxy, alkylthio, cycloalkyl, aryl, heterocyclyl, aralkyl or heterocyclylalkyl groups;

$R^3$ alkyl, alkenyl, alkynyl, cycloalkyl, aryl, heterocyclyl, aralkyl, heterocyclylalkyl, —CO—O—$R^9$, —CO—$R^{10}$, —SO—$R^{11}$, —$SO_2$—$R^{12}$;

$R^9$, $R^{10}$, $R^{11}$ and $R^{12}$ are alkyl, haloalkyl, alkenyl, alkynyl, cycloalkyl, aryl, heterocyclyl, aralkyl or heterocyclylalkyl, which groups $R^3$, $R^9$, $R^{10}$, $R^{11}$ and $R^{12}$ are optionally substituted by one or more halogen atoms, hydroxyl, oxo, alkyl, alkoxy, alkylthio, cycloalkyl, aryl, heterocyclyl or aralkyl groups, $R^4$ is halogen or —$NR^{13}R^{14}$, $R^{13}$ and $R^{14}$ are independently of one another hydrogen, alkyl, alkenyl, alkynyl, cycloalkyl, aryl, heterocyclyl, aralkyl or heterocyclylalkyl or $R^{13}$ and $R^{14}$ together with the attached N-atom form a five- to seven-membered heterocyclic ring which optionally contains an additional oxygen, sulfur or nitrogen atom in the ring, which groups $R^{13}$ and $R^{14}$ are optionally substituted by one or more halogen atoms, hydroxyl, oxo, alkyl, alkoxy, alkylthio, cycloalkyl, aryl, heterocyclyl, aralkyl or heterocyclylalkyl groups;

$R^5$ haloalkyl, haloalkoxy, or halogen, and n is an integer selected from 0, 1 or 2.

2. A compound of formula I according to claim 1 or a pesticidally acceptable salt thereof, wherein W is $CR^6$ or $C(NH_2)$.

3. A compound of formula I according to claim 1 or a pesticidally acceptable salt thereof, wherein $R^6$ is chlorine or fluorine.

4. A compound of formula I according to claim 1 or a pesticidally acceptable salt thereof, wherein $R^1$ is cyano, or —CS—$NH_2$.

5. A compound of formula I according to claim 1 or a pesticidally acceptable salt thereof, wherein $R^2$ is alkyl or haloalkyl.

6. A compound of formula I according to claim 1 or a pesticidally acceptable salt thereof, wherein $R^4$ is —$NR^{13}R^{14}$, fluorine, chlorine or bromine.

7. A compound of formula I according to claim 1 or a pesticidally acceptable salt thereof, wherein $R^5$ is —$CF_3$ or —O—$CF_3$.

8. A compound of formula I according to claim 1 or a pesticidally acceptable salt thereof wherein $R^1$ is CN, or —CS—$NH_2$, $R^2$ is $(C_1$-$C_3)$-alkyl or $(C_1$-$C_3)$-haloalkyl, W is C(halogen), CH, or $C(NR^7R^8)$, $R^4$ halogen, $R^5$ is —$CF_3$ or —O—$CF_3$, $R^7$ is hydrogen, $(C_1$-$C_6)$-alkyl, $(C_1$-$C_6)$-haloalkyl, $(C_2$-$C_6)$-alkenyl, or $(C_2$-$C_6)$-alkynyl, $R^8$ is $(C_1$-$C_4)$-haloalkyl or $(C_1$-$C_4)$-alkyl, or $R^7$ and $R^8$ together with the attached N atom form a five- to seven-membered saturated or unsaturated ring which optionally contains an additional hetero atom in the ring which is selected from O, S and N, the ring being unsubstituted or substituted by one or more radicals selected from the group consisting of halogen, $(C_1$-$C_6)$-alkyl, $(C_1$-$C_6)$-haloalkyl, $(C_1$-$C_6)$-alkoxy and oxo, which groups $R^7$ and $R^8$ independently of one another are optionally substituted by one or more halogen atoms, hydroxyl, oxo, cyano, nitro, alkyl, alkoxy, alkylthio, cycloalkyl, aryl, heterocyclyl, aralkyl or heterocyclylalkyl groups or by amino, which is optionally substituted by alkyl, alkenyl, alkynyl, aryl or heteroaryl groups.

9. A compound of formula I according to claim 1 a pesticidally acceptable salt thereof, wherein $R^1$ is —CN, $R^2$ is $(C_1$-$C_3)$-haloalkyl, W is C(halogen), $R^3$ is $(C_1$-$C_6)$-alkyl optionally substituted by one or more halogen atoms, hydroxyl, oxo, alkyl, alkoxy, alkylthio, cycloalkyl, aryl, heterocyclyl or aralkyl groups, $R^4$ is halogen or $-NR^{13}R^{14}$,
$R^5$ is $-CF_3$,
$R^{13}$ is hydrogen or $(C_1-C_3)$-alkyl, and
$R^{14}$ is $(C_1-C_3)$-alkyl optionally substituted with one or more of halogen atoms, hydroxyl, oxo, alkyl, alkoxy, alkylthio, cycloalkyl, aryl, heterocyclyl, aralkyl or heterocyclylalkyl groups.

10. A compound of formula I according to claim 9 or a pesticidally acceptable salt thereof, wherein
$R^1$ is $-CN$,
$R^2$ is $-CF_3$,
W is C(Cl),
$R^3$ is methyl,
$R^4$ is $-Cl$, and
$R^5$ is $-CF_3$.

11. A pesticidal composition comprising as an active ingredient at least one compound of formula I according to claim 1 or a pesticidally acceptable salt thereof.

12. A pesticidal composition according to claim 11 comprising diluents and/or carriers and/or surface active agents which are compatible with said active ingredient.

13. A pesticidal composition according to claim 11 which is a veterinary medicament and which is adapted for oral administration.

* * * * *